US010019643B2

(12) United States Patent
Ogawa

(10) Patent No.: US 10,019,643 B2
(45) Date of Patent: Jul. 10, 2018

(54) MEASUREMENT APPARATUS AND PROGRAM

(71) Applicant: OLYMPUS CORPORATION, Shibuya-ku, Tokyo (JP)

(72) Inventor: Kiyotomi Ogawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/109,592

(22) Filed: Dec. 17, 2013

(65) Prior Publication Data

US 2014/0205150 A1 Jul. 24, 2014

(30) Foreign Application Priority Data

Jan. 22, 2013 (JP) .................................. 2013-009226

(51) Int. Cl.
*G06K 9/46* (2006.01)
*G01B 11/00* (2006.01)
(Continued)

(52) U.S. Cl.
CPC .......... *G06K 9/4633* (2013.01); *G01B 11/002* (2013.01); *G01B 11/14* (2013.01);
(Continued)

(58) Field of Classification Search
None
See application file for complete search history.

(56) References Cited

U.S. PATENT DOCUMENTS

| 6,063,023 A | 5/2000 | Sakiyama et al. |
| 2005/0111710 A1* | 5/2005 | Gritzky .................. A61B 8/467 382/128 |

(Continued)

FOREIGN PATENT DOCUMENTS

| JP | 10-248806 A | 9/1998 |
| JP | 11132740 A | 5/1999 |

(Continued)

OTHER PUBLICATIONS

Japanese Office Action (and English translation thereof) dated Sep. 6, 2016, issued in counterpart Japanese Application No. 2013-009226.

(Continued)

*Primary Examiner* — Vu Le
*Assistant Examiner* — Tracy Mangialaschi
(74) *Attorney, Agent, or Firm* — Holtz, Holtz & Volek PC

(57) ABSTRACT

A region-setting unit sets, in an image, a region based on one reference point designated by a user in the image or a predetermined region as an extraction region. An edge extraction unit extracts an edge of the subject based on an image of the extraction region. When a plurality of edges are extracted, a display control unit causes a line indicating the plurality of extracted edges to be displayed on a display unit together with the image. An edge selection unit selects a reference edge from among the plurality of extracted edges based on an instruction from the user. A three-dimensional coordinate calculation unit calculates three-dimensional coordinates corresponding to points in the image. A reference line calculation unit calculates a reference line on a space based on the three-dimensional coordinates corresponding to points constituting the reference edge.

7 Claims, 18 Drawing Sheets

(51) Int. Cl.
  *G01B 11/14* (2006.01)
  *G06T 7/13* (2017.01)
  *G06T 7/62* (2017.01)
  *A61B 1/00* (2006.01)

(52) U.S. Cl.
  CPC .................. *G06T 7/13* (2017.01); *G06T 7/62* (2017.01); *A61B 1/00009* (2013.01); *G06T 2207/10068* (2013.01); *G06T 2207/30108* (2013.01)

(56) References Cited

U.S. PATENT DOCUMENTS

| | | | |
|---|---|---|---|
| 2007/0225931 A1* | 9/2007 | Morse | G02B 23/2469 702/127 |
| 2009/0010511 A1* | 1/2009 | Gardner | G06T 7/0016 382/128 |
| 2009/0092278 A1* | 4/2009 | Doi et al. | 382/100 |
| 2012/0033105 A1* | 2/2012 | Yoshino | A61B 1/00009 348/239 |
| 2012/0249399 A1* | 10/2012 | Sato | 345/4 |
| 2013/0287288 A1* | 10/2013 | Bendall | 382/154 |

FOREIGN PATENT DOCUMENTS

| | | |
|---|---|---|
| JP | 2000205839 A | 7/2000 |
| JP | 2002230527 A | 8/2002 |
| JP | 2004-049638 A | 2/2004 |
| JP | 2005019544 A | 1/2005 |
| JP | 2005-204724 A | 8/2005 |
| JP | 2008206956 A | 9/2008 |
| JP | 2008-295512 A | 12/2008 |
| JP | 2009282379 A | 12/2009 |
| JP | 2010179023 A | 8/2010 |

OTHER PUBLICATIONS

Japanese Notice of Allowance dated May 9, 2017 issued in counterpart Japanese Application No. 2013-009226.

* cited by examiner

MEASUREMENT APPARATUS AND PROGRAM

BACKGROUND OF THE INVENTION

Field of the Invention

The present invention relates to a measurement apparatus that performs line referencing to calculate a spatial distance between one measurement point and a reference line. Further, the present invention relates to a program for causing a computer to perform as the present measurement apparatus.

Priority is claimed on Japanese Patent Application No. 2013-009226, filed Jan. 22, 2013, the content of which is incorporated herein by reference.

Description of Related Art

One measurement method using an industrial endoscope or the like includes line-based measurement for calculating a spatial distance between one measurement point and a reference line. For example, a measurement method of setting a reference straight line based on a first reference point and a second reference point designated by a user (manipulator) and calculating a length of a foot of a perpendicular taken down from a measurement point designated by the user to the reference straight line is disclosed in Japanese Unexamined Patent Application, First Publication No. H10-248806. In other words, a measurement method of obtaining a distance between a straight line and a point is disclosed in Japanese Unexamined Patent Application, First Publication No. H10-248806.

A measurement method of calculating a distance between a measurement point and a reference line using a curve based on positions of three or more reference points designated by a user and a shape coefficient as the reference line is disclosed in Japanese Unexamined Patent Application Publication No. 2005-204724. In other words, a measurement method of obtaining a distance between the curve and the point is disclosed in Japanese Unexamined Patent Application Publication No. 2005-204724.

SUMMARY OF THE INVENTION

A measurement apparatus according to a first aspect includes: an imaging unit that images a subject to generate image data; a display unit that displays an image based on the image data; a region-setting unit that sets, in the image, a predetermined region in the image or a region based on one reference point designated by a user as an extraction region from which an edge of the subject is extracted; an edge extraction unit that extracts the edge of the subject based on an image of the extraction region; a display control unit that causes a graphic indicating the extracted edge to be displayed on the display unit together with the image; an edge selection unit that selects a reference edge from among a plurality of extracted edges based on an instruction from the user when the plurality of edges are extracted; a three-dimensional coordinate calculation unit that calculates three-dimensional coordinates corresponding to points in the image; a reference line calculation unit that calculates a reference line on a space based on the three-dimensional coordinates corresponding to a plurality of points constituting the reference edge; a measurement point designation unit that designates a measurement point in the image; and a distance calculation unit that calculates a distance between the three-dimensional coordinate corresponding to the measurement point and the reference line.

According to a second aspect of the present invention, in the measurement apparatus according to the first aspect, the three-dimensional coordinate calculation unit may calculate three-dimensional coordinates corresponding to points in a predetermined range including the predetermined region in the image at a time point at which an instruction from the user for starting up a measurement function is input or at a time point at which an instruction from the user for acquiring a still image displayed on the display unit is input, and the region-setting unit may set the extraction region in the predetermined region.

According to a third aspect of the present invention, in the measurement apparatus according to the second aspect, the region-setting unit may further set a selection region from which the edge of the subject is selected, based on one reference point designated by the user in the image, the edge selection unit may select edges overlapping the selection region from among a plurality of edges when the plurality of edges are extracted, and select a reference edge from among the edges overlapping the selection region based on an instruction from the user, and the display control unit may cause lines indicating the edges overlapping the selection region to be displayed on the display unit together with the image.

According to a fourth aspect of the present invention, in the measurement apparatus according to the first aspect, when a plurality of edges are extracted, the display control unit may cause a graphic indicating the plurality of extracted edges and information of an order based on an index value of each edge to be displayed on the display unit together with the image.

According to a fifth aspect of the present invention, in the measurement apparatus according to the fourth aspect, the region-setting unit may further set a selection region from which the edge of the subject is selected, based on one reference point designated by the user in the image, and when a plurality of edges are extracted, the edge selection unit may select edges overlapping the selection region from among the plurality of edges, calculate the index values of the edges overlapping the selection region, and select a reference edge from among the edges overlapping the selection region based on an instruction from the user.

According to a sixth aspect of the present invention, in the measurement apparatus according to the first aspect, the edge extraction unit may further trace the edge of the subject based on an image of the outside of the extraction region for the extracted edge.

According to a seventh aspect of the present invention, a computer program product storing a program that causes a computer to perform steps of: setting, in an image based on image data generated by an imaging unit imaging a subject, a predetermined region in the image or a region based on a reference point designated by a user as an extraction region from which an edge of the subject is extracted; extracting the edge of the subject based on an image of the extraction region; causing a graphic indicating the extracted edge to be displayed on a display unit together with the image; selecting a reference edge from among a plurality of extracted edges based on an instruction from the user when the plurality of edges are extracted; calculating three-dimensional coordinates corresponding to points in the image; calculating a reference line on a space based on the three-dimensional coordinates corresponding to a plurality of points constituting the reference edge; designating a measurement point in the image; and calculating a distance between the three-dimensional coordinate corresponding to the measurement point and the reference line.

DETAILED DESCRIPTION OF THE INVENTION

Hereinafter, embodiments of the present invention will be described with reference to the drawings. Hereinafter, a method for line-based measurement using an endoscope device, which is an example of a measurement apparatus, will be described.

Figure 1:
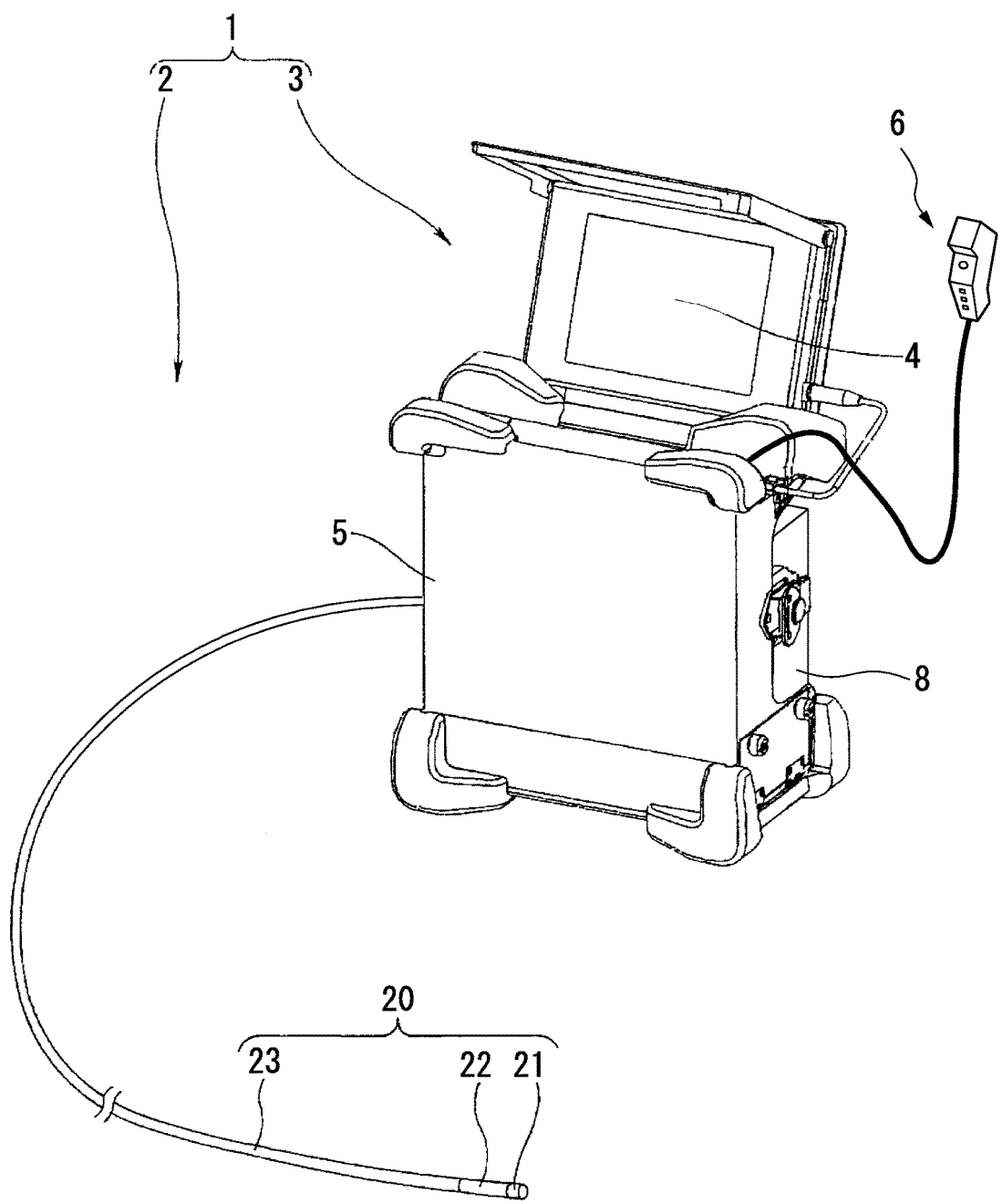
FIG. 1 is a perspective view illustrating an entire configuration of an endoscope device according to an embodiment of the present invention.

First, an embodiment of the present invention will be described. FIG. 1 illustrates an entire configuration of an endoscope device according to the present embodiment. The endoscope device 1 includes an endoscope unit 2, and a device body 3 connected to the endoscope unit 2, as shown in FIG. 1. The endoscope unit 2 includes an elongated insertion portion 20, and a connector unit 8 to which a base end portion of the insertion portion 20 is connected. The connector unit 8 includes a connector (not shown), and is connected to the device body 3 via the connector. The connector unit 8 is configured to be detachable from the device body 3. The device body 3 includes a monitor 4 (an LCD monitor) which is a display device that performs displaying of an image of a subject based on an image data obtained through imaging by the endoscope unit 2, manipulation control content (e.g., processing menus) and the like, and a housing 5 having a control unit 10 (see FIG. 2) provided therein. A manipulation unit 6 for performing necessary manipulations when various operation controls of the entire device are executed is connected to the device body 3.

The insertion portion 20 includes a hard tip portion 21, a bending portion 22 which can be bent, for example, vertically and horizontally, and a flexible tube portion 23 having flexibility, which are continuously provided in order from a tip side. Various optical adapters such as a stereo optical adapter having two observation fields of view or a normal observation optical adapter having one observation field of view are detachable from the tip portion 21.

Figure 2:
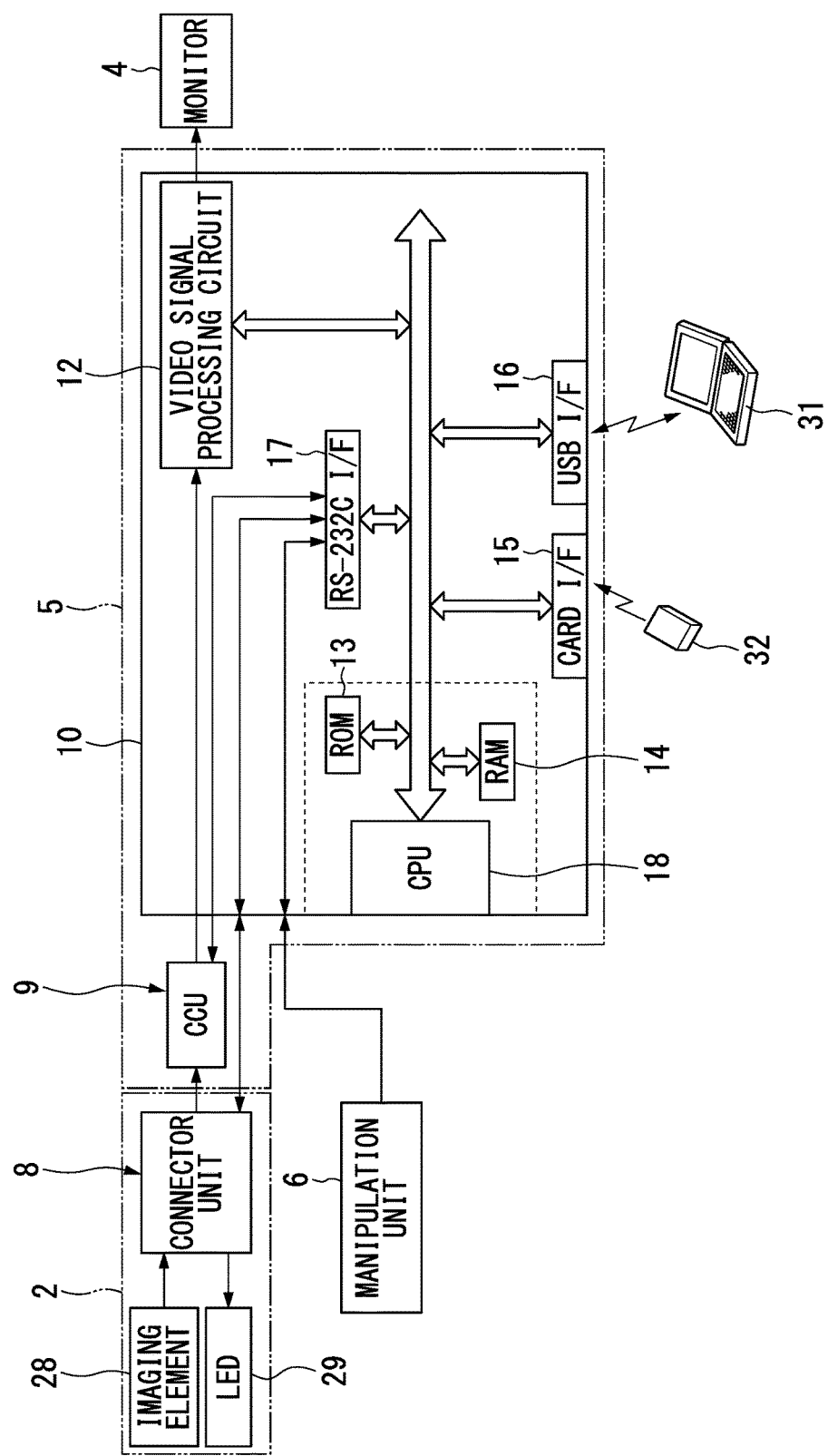
FIG. 2 is a block diagram illustrating an internal configuration of the endoscope device according to the embodiment of the present invention.

A CCU (camera control unit) 9 and a control unit 10 are provided in the housing 5, as shown in FIG. 2. The base end portion of the insertion portion 20 is connected to the connector unit 8, and the connector unit 8 is connected to the device body 3 via a connector. The connector unit 8 includes a light source-driving device that drives a light source built in the tip portion 21, and a bending device that bends the bending portion 22 constituting the insertion portion 20. The CCU 9 includes a driving device that drives an imaging element 28.

The imaging element 28 and an LED 29 are built in the tip portion 21. The imaging element 28 performs photoelectric conversion on a subject image formed through the optical adapter to generate an imaging signal. The imaging signal is converted, for example, to a video signal (image data) such as an NTSC signal in the CCU 9 and supplied to the control unit 10. The LED 29 generates illumination light radiated on the subject.

In the control unit 10, a video signal processing circuit 12 to which the video signal is input, a ROM 13, a RAM 14, a card I/F (card interface) 15, a USB I/F (USB interface) 16, an RS-232C I/F (RS-232C interface) 17, and a CPU 18 are provided.

The CCU 9 and the connector unit 8 are connected to the RS-232C I/F 17, while the manipulation unit 6 that performs controlling and manipulation instructing of the CCU 9 and the connector unit 8 or the like is also connected to the RS-232C I/F 17. If a user manipulates the manipulation unit 6, communication necessary when controlling the operation of the CCU 9 and the connector unit 8 is performed based on a content of the manipulation. A device for manipulation included in the manipulation unit 6 may be any of a mouse, a joy-stick, a touch pad, a track ball, and a touch panel.

The USB I/F 16 is an interface for electrically connecting the control unit 10 with a personal computer 31. By connecting the control unit 10 with the personal computer 31 via the USB I/F 16, control based on a display instruction for an endoscope image or various instructions such as image processing at the time of a measurement can be performed on the side of the personal computer 31, and input and output of control information, data or the like necessary for various processes between the control unit 10 and the personal computer 31 can be performed.

Further, a memory card 32 may be freely attached to or detached from the card I/F 15. By attaching the memory card 32 to the card I/F 15, either acquisition of data such as control processing information and image information stored in the memory card 32 to the control unit 10 or recording of the data such as control processing information or image information in the memory card 32 may be performed under control of the CPU 18.

The video signal processing circuit 12 performs a process of combining a graphic image signal based on a manipulation menu which is generated by the CPU 18, with the video signal from the CCU 9 in order to display a combination image obtained by combining the endoscope image based on the video signal supplied from the CCU 9 with a graphic manipulation menu, a process necessary for display on a screen of the monitor 4 or the like, and supplies a display signal to the monitor 4. Further, the video signal processing circuit 12 may merely perform a process for displaying the endoscope image or an image such as a manipulation menu alone. Therefore, the endoscope image, the manipulation menu image, the combination image of the endoscope image with the manipulation menu image, or the like is displayed on the screen of the monitor 4.

The CPU 18 controls various circuit portions or the like to perform a process according to their purpose by executing a program such as a measurement program stored in the ROM 13, to control an entire operation of the endoscope device 1. The RAM 14 is used as a working area for temporary data storage by the CPU 18.

The program executed by the CPU 18 may be recorded in a computer-readable recording medium, and the program recorded in this recording medium may be loaded to and executed by a computer rather than the endoscope device 1. For example, the personal computer 31 may load and execute the program, transmit control information for controlling the endoscope device 1 to the endoscope device 1 to control the endoscope device 1 according to the program, acquire a video signal from the endoscope device 1, and perform a measurement using the acquired video signal.

Here, the "computer" may also include a homepage providing environment (or display environment) if a WWW system is being used. Also, the "computer-readable recording medium" includes a portable medium such as a flexible disk, a magnetic optical disc, a ROM, a CD-ROM, a DVD-ROM or a flash memory, or a storage device such as a hard disk installed in a computer. Further, the "computer-readable recording medium" may also include a recording medium that holds a program for a certain time, such as a volatile memory (a RAM) inside a computer system including a server and a client when a program is transmitted via a network such as the Internet or a communication line such as a telephone line.

Further, the above-described program may be transmitted from a computer in which the program is stored in a storage device or the like to other computers via a transmission medium or by transmission waves in the transmission medium. Here, the "transmission medium" for transmitting the program refers to a medium having a function of transmitting information, like a network (communication network) such as the Internet or a communication line such as a telephone line. Also, the above-described program may be a program for realizing some of the above-described functions. Alternatively, the program may be a program capable of realizing the above-described functions in combination with a program previously recorded in a computer system, i.e., a so-called differential file (a differential program).

In the present embodiment, a line-based measurement based on stereo measurement using a principle of triangulation will be described for example. The line-based measurement may be performed using a measurement method other than the stereo measurement. For example, the line-based measurement may be performed using a stripe projection method using parallel stripes consisting of a bright portion and a dark portion.

Figure 21:
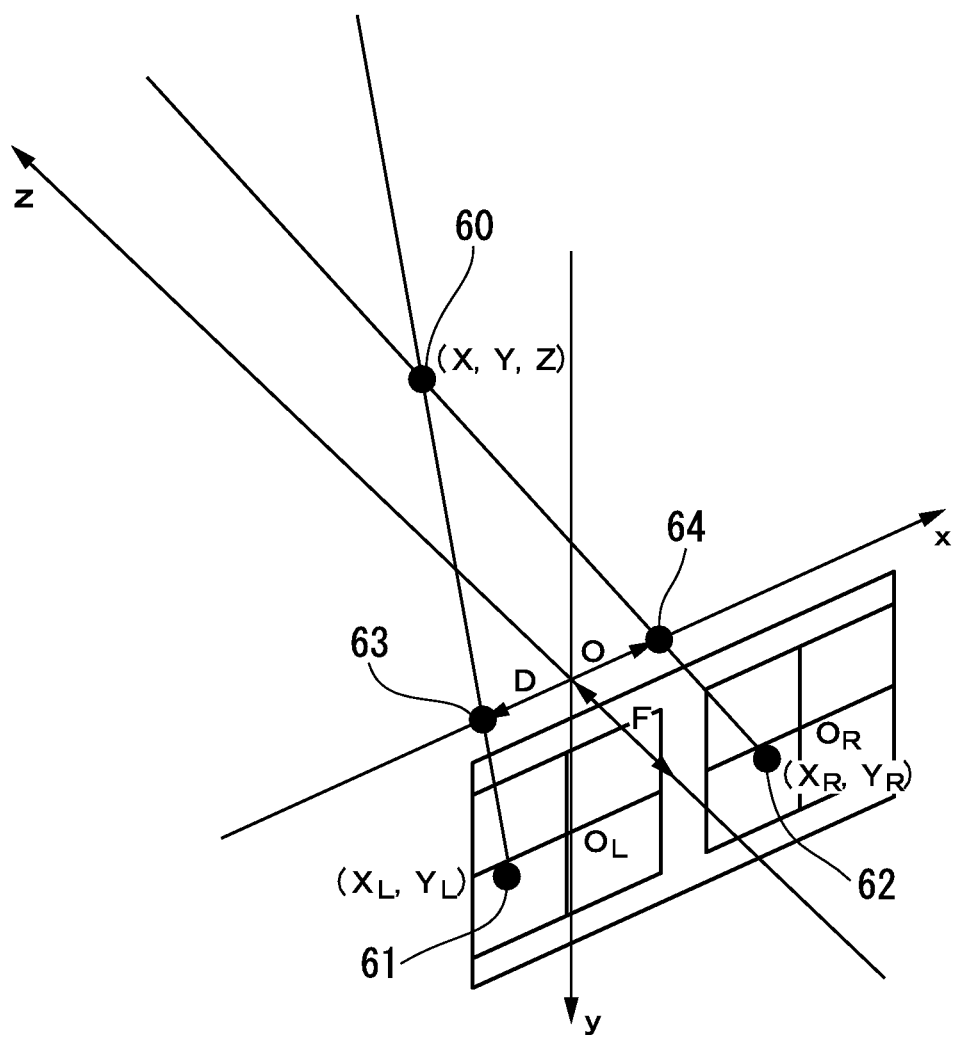
FIG. 21 is a reference diagram illustrating a method of obtaining three-dimensional coordinate of a measurement point through stereo measurement.

Hereinafter, a principle of the stereo measurement will be described. In the stereo measurement, first, a two-dimensional coordinate on an image plane of a corresponding point corresponding to a measurement point is obtained from a two-dimensional coordinate on an image plane of the measurement point through a matching process. Also, a three-dimensional coordinate of the measurement point is calculated from the two-dimensional coordinates on the image plane of the measurement point and the corresponding point, and is used for calculation of an area or a peripheral length. Hereinafter, a method of obtaining the three-dimensional coordinate of the measurement point through the stereo measurement will be described with reference to FIG. 21. A three-dimensional coordinate (X, Y, Z) of a measurement point 60 when a middle point of a line connecting left and right optical centers 63 and 64 is an origin O, a right direction is defined as a positive x-axis, a down direction is defined as a positive y-axis, and a direction away from the optical system in parallel with an optical axis is defined as a positive z-axis is calculated by the following Equations (1) to (3) using a triangulation method for an image obtained through imaging in the left and right optical systems. Here, two-dimensional coordinates of the measurement point 61 and the corresponding point 62 on the left and right image planes subjected to distortion correction are $(X_L, Y_L)$ and $(X_R, Y_R)$, with intersections $O_L$ and $O_R$ between optical axes of the left and right optical systems and the left and right image planes being origins, a distance between the left and right optical centers 63 and 64 is D, a focal distance is F, and $t=D/(X_R-X_L)$.

$$X = t \times X_R + D/2 \tag{1}$$

$$Y = -t \times Y_R \tag{2}$$

$$Z = t \times F \tag{3}$$

If the coordinates of the measurement point 61 and the corresponding point 62 on the image planes on an original image are determined as described above, a three-dimensional coordinates of the measurement point 60 is obtained using the parameters D and F. Various measurements of a distance between two points, a distance between a line connecting two points and one point, an area, a depth, a surface shape and the like may be performed by obtaining three-dimensional coordinates of some points. Further, a distance from the left optical center 63 or the right optical center 64 to a subject (an object distance) may also be obtained. The object distance is a distance from the tip portion 21 to the subject and, for example, is a distance from the imaging element 28 or the observation optical system to the subject. Optical data indicating characteristics of the optical system including the tip portion 21 and the stereo optical adapter is necessary to perform the stereo measurement described above. Since details of the matching process and the optical data are described, for example, in Japanese Unexamined Patent Application, First Publication No. 2004-49638, a description thereof is omitted.

Figure 3:
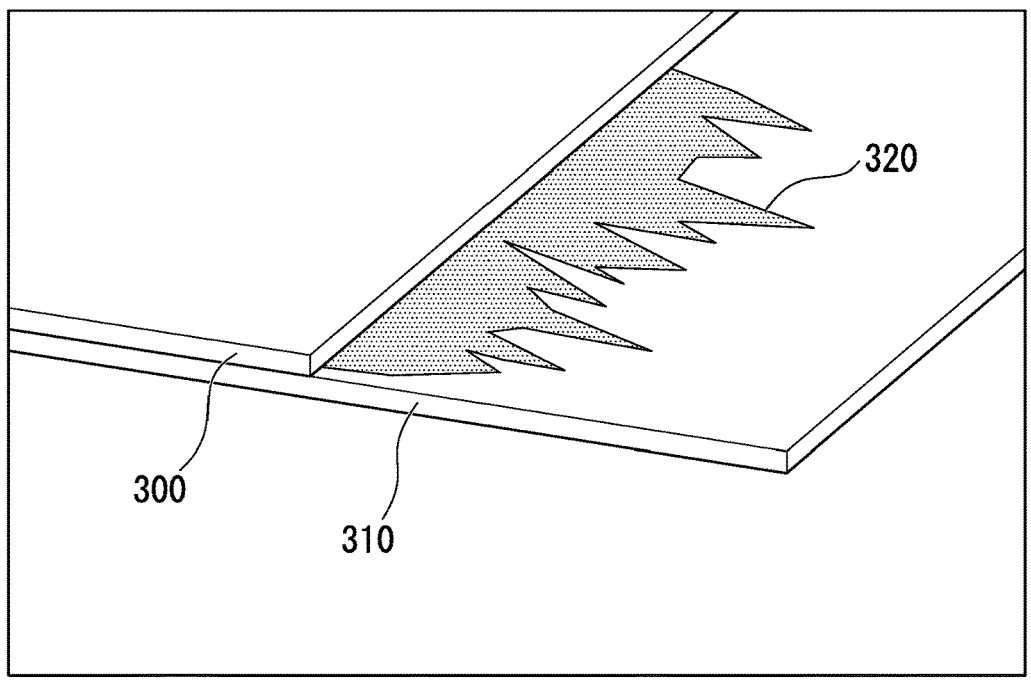
FIG. 3 is a reference view illustrating an image of a subject according to the embodiment of the present invention.

Next, an overview of the line-based measurement in the present embodiment will be described. FIGS. 3 to 6 illustrate images (still images) of the subject. FIG. 3 illustrates an image obtained through imaging. In the following example, a width of an adhesive 320 protruding from an interval between two plates 300 and 310 when the two plates 300 and 310 are bonded with the adhesive is measured.

Figure 4:
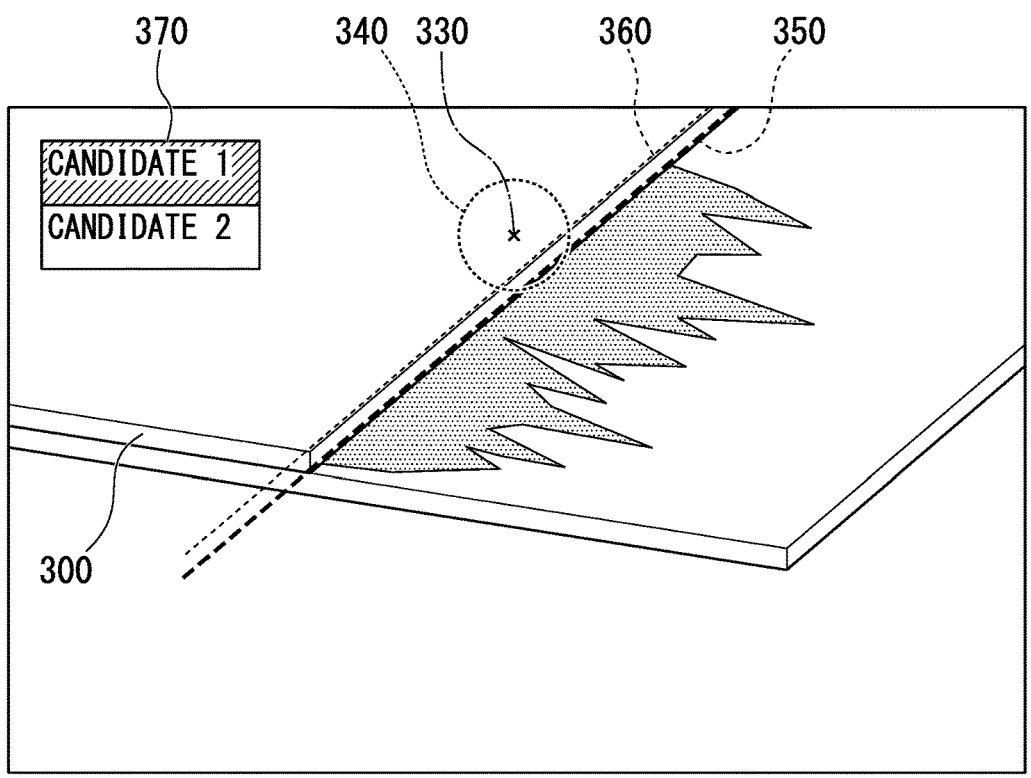
FIG. 4 is a reference view illustrating an image of a subject according to the embodiment of the present invention.

FIG. 4 illustrates an image displayed on the monitor 4 while the line-based measurement is being performed. When the user manipulates the manipulation unit 6 to designate, as a reference point, a position close to a position (e.g., an edge of the plate 300) in which a reference line is desired to be set, a region inside a circle 340 having a radius of a predetermined value (e.g., 20 pixels) around a coordinate (a two-dimensional coordinate in the image) of the designated reference point 330 is set as an edge extraction region. The edge extraction region is a region in which a process of extracting an edge by using image processing is performed. The predetermined value described above may be appropriately changed. The reference point 330 designated by the user and the circle 340 indicating the edge extraction region may or may not be displayed on the image.

Subsequently, an edge is extracted inside the edge extraction region. Further, a process of tracing the edge on an image outside the edge extraction region is performed on the edge extracted in the edge extraction region. Accordingly, an edge which is an extension portion of the edge extracted in the edge extraction region is extracted. Also, a graphic indicating the extracted edge is displayed as a line on the image. In FIG. 4, lines 350 and 360 are displayed. As the process of tracing an edge is performed, the edge extracted in the circle 340 corresponding to the edge extraction region extends to the outside of the circle 340.

When a plurality of edges are extracted, an index value is calculated for each edge, and an order of the edges is determined according to the index value. An order information of the determined order is displayed on the image. In FIG. 4, an order information 370 indicating the order of the edges corresponding to the lines 350 and 360 is displayed. The order information 370 indicates the order (candidate 1) of the edge corresponding to the line 350 and the order (candidate 2) of the edge corresponding to the line 360. The order information 370 is displayed as an icon (mark). In FIG. 4, the edge corresponding to the line 350 is in higher order than the edge corresponding to the line 360.

A line corresponding to an edge selected as the reference edge which is the edge corresponding to the reference line among a plurality of edges is displayed to be emphasized more than lines corresponding to other edges. In a state immediately after the plurality of edges have been extracted, a line corresponding to an edge which is in highest order is displayed to be emphasized. In FIG. 4, the line 350 corresponding to the edge which is in highest order is displayed more thickly than the line 360. Further, in order to present the order of the edge corresponding to the emphasized line to the user, information corresponding to the emphasized line 350 in the order information 370 is displayed to be emphasized (e.g., with a different color). In FIG. 4, the edge corresponding to the line 350 is selected as the reference edge.

Figure 5:
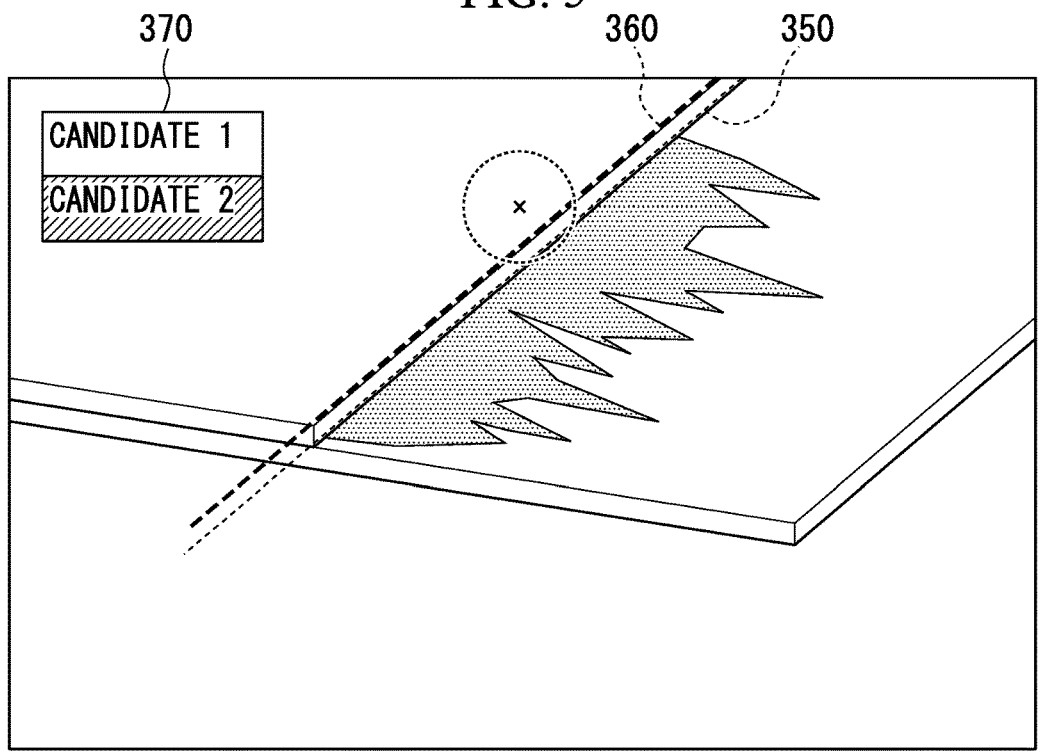
FIG. 5 is a reference view illustrating an image of a subject according to the embodiment of the present invention.

The user can switch the edge to be selected as the reference edge by manipulating the manipulation unit 6. When switching the edge, the user need not directly designate an edge using a pointing cursor or the like, and need only input a trigger for switching the edge. When the user performs a manipulation to switch the edge, for example, the line corresponding to the edge currently being selected as the reference edge is displayed in a normal state, and a line corresponding to an edge which is 1 order lower than the edge is emphasized. FIG. 5 illustrates an image displayed on the monitor 4 after the user switches the edge. The line 360 corresponding to an edge in lower order is displayed more thickly than the line 350. Further, in the order information 370, information corresponding to the emphasized line 360 is displayed to be emphasized (e.g., with a different color). In FIG. 5, the edge corresponding to the line 360 is selected as the reference edge.

When the user manipulates the manipulation unit 6 to perform a decision manipulation in a state in which a desired edge is selected as the reference edge, the reference edge is decided. For example, if the decision manipulation is performed in the state of FIG. 4, the edge corresponding to the line 350 is treated as the reference edge in a subsequent process, and if the decision manipulation is performed in the state of FIG. 5, the edge corresponding to the line 360 is treated as the reference edge in the subsequent process. After the reference edge is decided, a three-dimensional coordinate corresponding to each pixel included in the reference edge on the image are calculated, and an equation of a straight line or a curve which is the reference line corresponding to the reference edge is calculated based on the three-dimensional coordinates.

Figure 6:
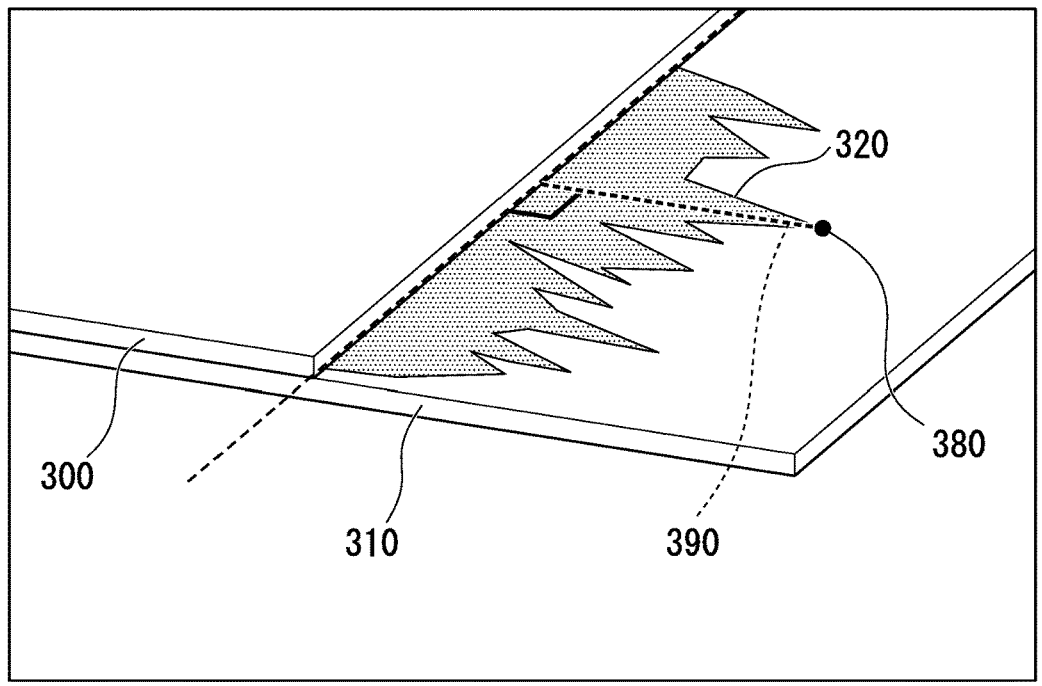
FIG. 6 is a reference view illustrating an image of a subject according to the embodiment of the present invention.

After the reference edge is decided, the user manipulates the manipulation unit 6 to designate a measurement point in line-based measurement. FIG. 6 illustrates the measurement point designated by the user and a measurement position of the line-based measurement. In FIG. 6, a measurement point 380 is designated in a position of a vertex of the adhesive 320 protruding from between plates 300 and 310.

When the measurement point is designated, a three-dimensional coordinates corresponding to the measurement point is calculated and a three-dimensional distance between the measurement point and the reference line is calculated. In FIG. 6, the three-dimensional distance corresponding to a length of a line 390 is calculated as the three-dimensional distance between the measurement point and the reference line. The calculated three-dimensional distance is displayed on the monitor 4.

In line-based measurement of related art, it is necessary to designate two or more reference points in order to set a reference line, and a user should perform a manipulation such as a manipulation for enlarging and displaying an image when designating each reference point, and perform a manipulation for designating positions of the reference points while carefully monitoring positions in which reference points are to be set. On the other hand, in the line-based measurement of the present embodiment, manipulations necessary to set the reference line may be only a manipulation for designating one reference point in order to set the edge extraction region, and a manipulation for selecting the reference edge from among a plurality of extracted edges. The user need not carefully monitor a position in which the reference point is to be set when designating the one reference point, and may designate the reference point in an approximate position. Further, the user may perform only a simple manipulation such as a manipulation for inputting a trigger for switching an edge to be selected as the reference edge when selecting the reference edge. Therefore, time and effort of the manipulation related to setting of the reference line can be reduced and time necessary for the line-based measurement can be shortened.

Figure 7:
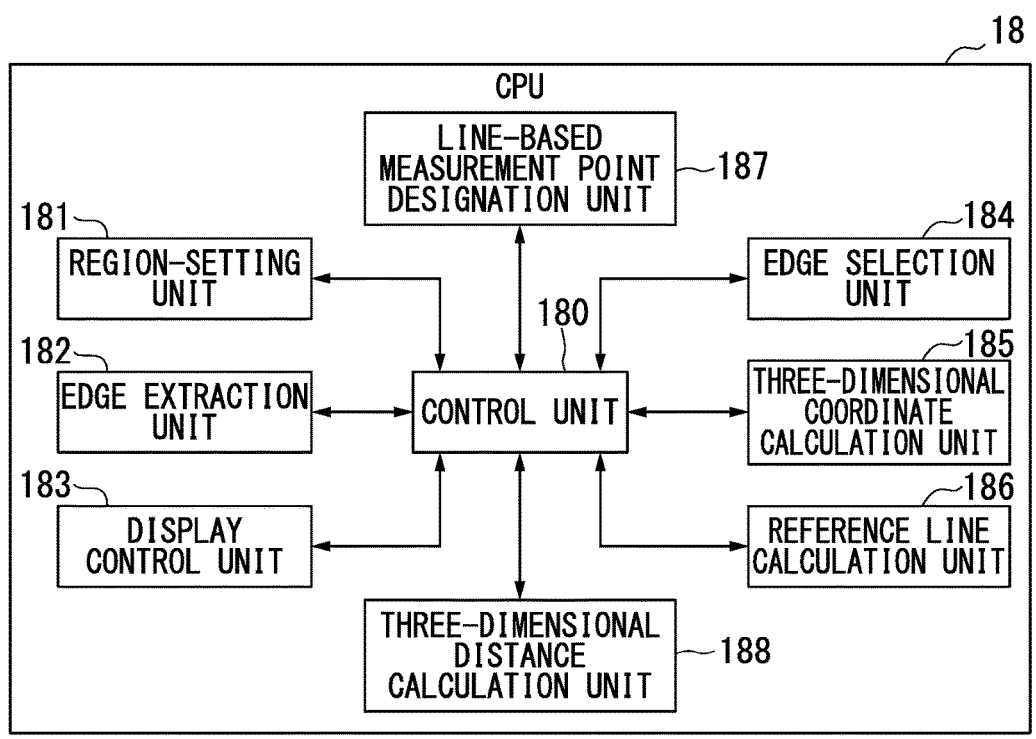
FIG. 7 is a block diagram illustrating a functional configuration of a CPU included in the endoscope device according to the embodiment of the present invention.

Next, details of the line-based measurement in the present embodiment will be described. FIG. 7 illustrates a functional configuration of the CPU 18. A function of the CPU 18 is realized by a control unit 180, a region-setting unit 181, an edge extraction unit 182, a display control unit 183, an edge selection unit 184, a three-dimensional coordinate calculation unit 185, a reference line calculation unit 186, a line-based measurement point designation unit 187, and a three-dimensional distance calculation unit 188.

The control unit 180 controls a process performed by each unit. The region-setting unit 181 sets, in an image of a subject, the edge extraction region based on a reference point designated by the user in the image of the subject based on image data acquired by the CPU 18 through the video signal processing circuit 12. The edge extraction unit 182 extracts the edge of the subject based on the image of the edge extraction region. The display control unit 183 performs controlling to cause information necessary for line-based measurement (e.g., the reference point 330, the circle 340, the lines 350 and 360, and the order information 370 of FIG. 4, and the measurement point 380 of FIG. 6) to be graphically displayed on the monitor 4

The edge selection unit 184 selects a reference edge from among a plurality of edges extracted by the edge extraction unit 182, based on an instruction from the user input through the manipulation unit 6. The three-dimensional coordinate calculation unit 185 calculates a three-dimensional coordinate corresponding to a point on the image of the subject through stereo measurement. The reference line calculation unit 186 calculates a reference line on a space based on the three-dimensional coordinates corresponding to the points constituting the reference edge. The line-based measurement point designation unit 187 designates a measurement point in the line-based measurement based on an instruction from the user input through the manipulation unit 6. The three-dimensional distance calculation unit 188 calculates the three-dimensional distance between the three-dimensional coordinate corresponding to the measurement point and the reference line.

Figure 8:
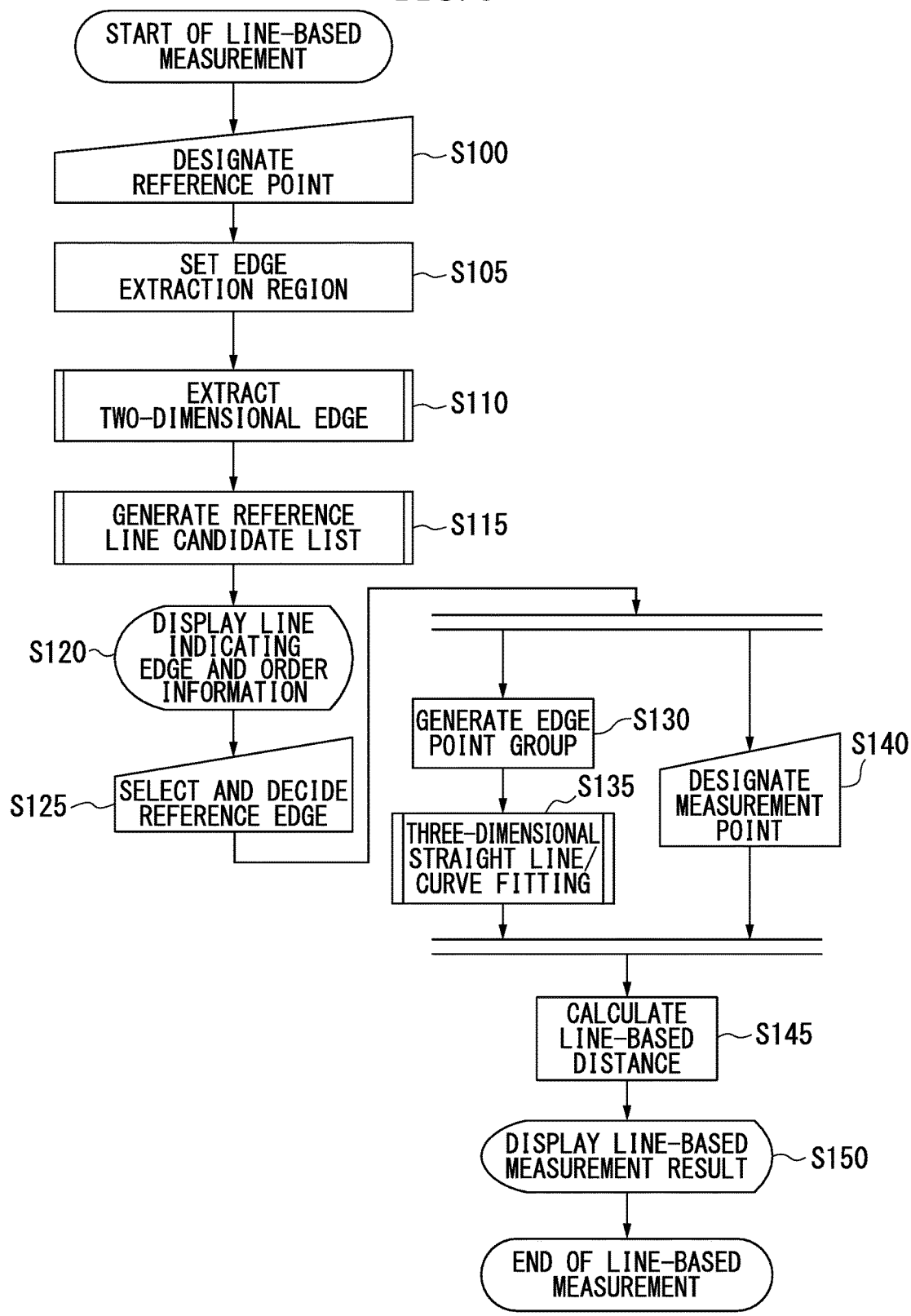
FIG. 8 is a flowchart illustrating a flow of a line-based measurement process according to the embodiment of the present invention.

FIG. 8 illustrates a flow of a process in the line-based measurement. Hereinafter, details of the process in the line-based measurement will be described. If the line-based measurement is initiated after a still image of the subject is acquired according to an instruction from the user, the manipulation unit 6 is manipulated by the user, and the reference point that is a reference for setting the edge extraction region is designated on the image (step S100). If the reference point is designated, the region-setting unit 181 sets the edge extraction region based on the reference point on the image (step S105). A region inside a circle having a radius of a predetermined value around a two-dimensional coordinate of the reference point is set as the edge extraction region, as described above. The edge extraction region may be the region set on the basis of the coordinate of the reference point, and need not necessarily be a circle.

Figure 9:
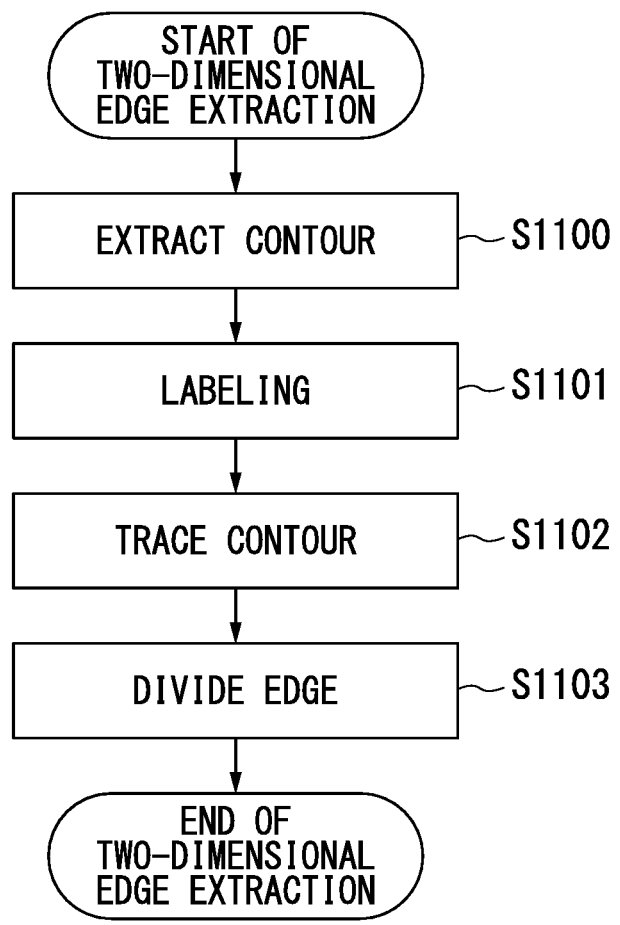
FIG. 9 is a flowchart illustrating a flow of a two-dimensional edge extraction process according to the embodiment of the present invention.

If the edge extraction region is set, the edge extraction unit 182 performs two-dimensional edge extraction to extract an edge from the two-dimensional image (step S110). FIG. 9 illustrates a flow of a two-dimensional edge extraction process in step S110. When a processing target image is a color image, the edge extraction unit 182 converts the color image to a gray scale and performs contour extraction on an image of the edge extraction region in the image after the conversion, using a Canny edge detector, to extract an edge (step S1100). The Canny edge detector is described in, for example, "J. E Canny: A Computational Approach to Edge Detection, in IEEE Transaction Pattern Analysis Machine Intelligence, Vol. 8, No. 6, pp. 679-698 (1986)."

Subsequently, the edge extraction unit 182 performs labeling using a raster scan and a look-up table on the extracted edge (step S1101). Accordingly, a label of each edge is given to the extracted edge. The labeling using the raster scan and the look-up table is described, for example, in "Digital Image Processing, Computer Graphic Arts Society (CG-ARTS Society), Incorporated Foundation, p 181-182."

Then, the edge extraction unit 182 performs contour tracing using the image of the outside of the edge extraction region to extract an edge of an extension portion of the edge extracted in step S1100 (step S1102). The contour tracing is described, for example, in "Digital Image Processing, Computer Graphic Arts Society (CG-ARTS Society), Incorporated Foundation, p 178-179." Further, for the contour tracing, a method described in Japanese Unexamined Patent Application, First Publication No. 2008-295512 may be used. Two-dimensional coordinates of points (pixels) constituting the edge extracted in steps S1100 and S1102 are managed as an edge data together with the label. The edge data is stored in the RAM 14 and appropriately read by the CPU 18.

Then, the edge extraction unit 182 divides the edge extracted in steps S1100 and S1102 (step S1103). Hereinafter, details of a process of dividing the edge will be described. When the image of the subject is an xy plane, a vector p on the xy plane is represented by the following Equation (4) as a linear combination of a vector a parallel to an x-axis and a vector b orthogonal to the vector a and parallel to a y-axis ($x\_p$ and $y\_p$ are an x component and a y component of the vector p, respectively).

$$p = x\_p a + y\_p b \tag{4}$$

Further, the vector p is represented by the following Equation (5) as a linear combination of any two vectors u and v orthogonal to each other on the xy plane.

$$p = su + tv \tag{5}$$

s and t in Equation (5) denote u and v components of the vector p, respectively. Here, when an x component and a y component of the vector u are $x\_u$ and $y\_u$ and an x component and a y component of the vector v are $x\_v$ and $y\_v$, the vectors u and v are represented by the following Equations (6) and (7).

$$u = x\_u a + y\_u b \tag{6}$$

$$v = x\_v a + y\_v b \tag{7}$$

From Equations (5) to (7), the vector p is represented by the following Equation (8).

$$p = su + tv \quad (8)$$
$$= s(x\_ua + y\_ub) + t(x\_va + y\_vb)$$
$$= (sx\_u + tx\_x)a + (sy\_u + ty\_v)b$$

From Equation (8), Equations (9) and (10) are established.

$$x\_p = sx\_u + tx\_v \quad (9)$$

$$y\_p = sy\_u + ty\_v \quad (10)$$

Equations (9) and (10) can be solved as a simultaneous equation for s and t, and and t are a u component and a v component, respectively, when the vector p is represented by vectors u and v. In other words, a representation of the vector p (Equation (4)) in a predetermined direction on the xy plane represented by the x component and the y component may be changed into a representation using the vectors u and v.

When the edge is divided, the edge extraction unit 182 obtains a tangential direction of the edge at each point (pixel) on the edge and obtains a vector indicating a change of the tangential direction at each point from tangential directions at points on both sides of each point on the edge. When a unit vector parallel to a tangential direction at any point i on the edge is $q_i$, a vector indicating the change of the tangential direction at the point i is $p_i$, and the points on both sides of the point i are a point i−1 and a point i+1, the vector $p_i$ indicating the change of the tangential direction is represented by the following Equation (11).

$$p_i = q_{i+1} - q_{i-1} \quad (11)$$

The vector indicating the change of the tangential direction at each point on the edge may be represented by a vector (corresponding to the vector u described above) parallel to the tangential direction and a vector (corresponding to the vector v described above) perpendicular to the tangential direction. The edge extraction unit 182 obtains a component of the vector parallel to the tangential direction and a component of the vector perpendicular to the tangential direction, in the vector indicating the change of the tangential direction of each point on the edge. The edge extraction unit 182 then divides the edge in pixels of which the component of the vector perpendicular to the tangential direction exceeds a predetermined value or in pixels of which the sign of such a component is reversed. The respective divided edges become into different edges, and different labels are given to each edge. Here, the divided edges have no inflection points. Edge data for managing coordinates of points constituting the edge and the labels of the edges is updated to be data corresponding to each divided edge. If the edge is divided, the two-dimensional edge extraction process ends.

Figure 10:
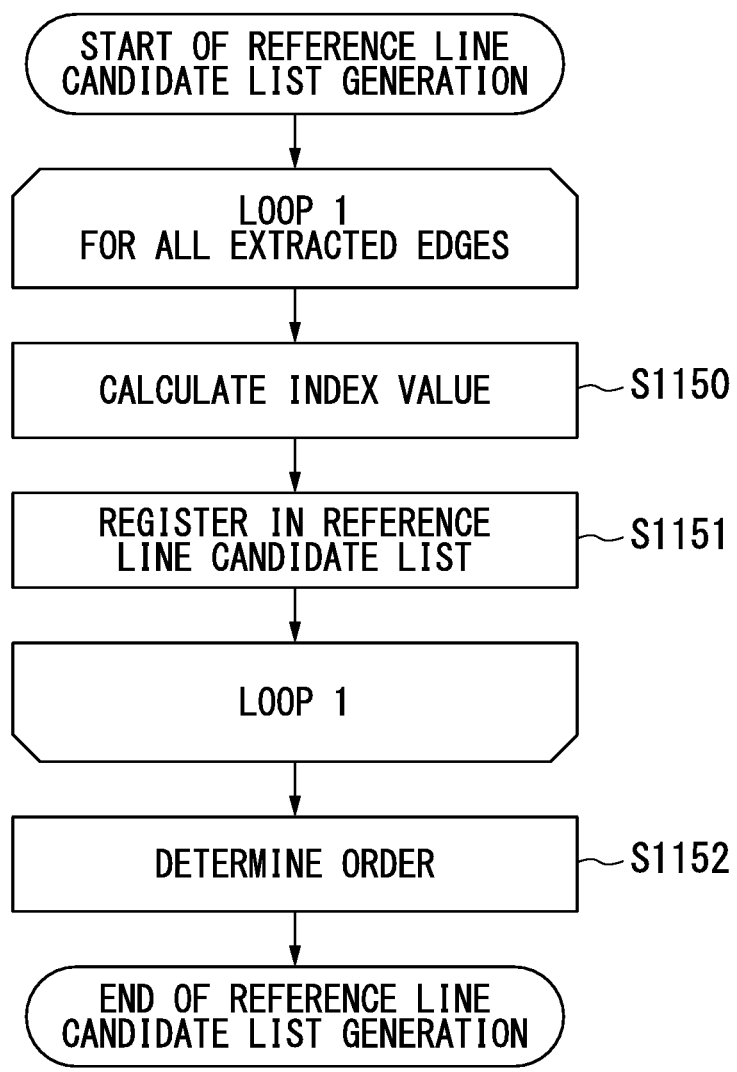
FIG. 10 is a flowchart illustrating a flow of a process of generating a reference line candidate list according to the embodiment of the present invention.

When the two-dimensional edge extraction process ends, the edge extraction unit 182 generates a reference line candidate list including index values of the edges extracted in step S110 (including the edges after the division) (step S115). FIG. 10 illustrates a flow of a process of generating the reference line candidate list in step S115. The edge extraction unit 182 performs a process of steps S1150 and S1151 on all the edges extracted in step S110 (including the edges after the division).

First, the edge extraction unit 182 calculates an index value of each edge (step S1150). The index value is strength (contrast) of the edge, a length of the edge, a radius of curvature of the edge, or the like.

Other values may be used as the index value. It is more preferable for the index value to be such a value that the accuracy of a measurement result when the three-dimensional distance is measured is expected to be higher as the value is greater. When an edge having high strength is used as the reference edge, a three-dimensional reference line well fit to the three-dimensional coordinates of each of points constituting the reference edge is easily obtained and a measurement result can be obtained with higher accuracy. The edge extraction unit 182 then registers the index value of each edge in the reference line candidate list (step S1151). The reference line candidate list is stored in the RAM 14 and appropriately read by the CPU 18.

After the process of steps S1150 and S1151 is performed on all the edges extracted in step S110, the edge extraction unit 182 determines an order of the edges based on the index value of each edge (step S1152). The order of the edges is, for example, descending order of the index value. Information of the order of the edges may be registered in the reference line candidate list or may be managed separately from the reference line candidate list. When the order of the edges is determined, the process of generating a reference line candidate list ends.

When the process of generating a reference line candidate list ends, the display control unit 183 generates a graphic image signal for causing the line indicating each extracted edge and the order information to be displayed on the monitor 4 based on the edge data and the reference line candidate list, and outputs the graphic image signal to the video signal processing circuit 12. Accordingly, the line indicating each extracted edge and the order information are displayed on the monitor 4 to be superimposed on the image (step S120), for example, as shown in FIG. 4. The user may confirm which of the extracted edges is optimal as the reference edge based on the image displayed on the monitor 4.

After the line indicating each extracted edge and the order information are displayed, the manipulation unit 6 is manipulated by the user and the reference edge is selected. In this case, the user can switch the edge to be selected as the reference edge, as described above. The edge selection unit 184 performs a process of selecting data of the edge selected as the reference edge from among data included in the edge data based on an instruction from the user input via the manipulation unit 6, notifying the display control unit 183 of the data, and emphasizing the line corresponding to the edge selected as the reference edge. When a decision manipulation is performed by the user in a state in which a desired edge is selected as the reference edge, the reference edge is decided (step S125).

After the reference edge is decided, a process of steps S130 and S135 and a process of step S140 are performed concurrently. The three-dimensional coordinate calculation unit 185 calculates the three-dimensional coordinate corresponding to each of points constituting the reference edge to generate an edge point group consisting of the three-dimensional coordinates of the respective points (step S130). Then, the reference line calculation unit 186 performs three-dimensional straight line/curve fitting to apply a straight line or a curve on a space to the edge point group and calculates an equation (approximation equation) of the straight line or the curve (step S135). The calculated straight line or curve is the reference line.

In parallel with the process of steps S130 and S135, the manipulation unit 6 is manipulated by the user and a measurement point in the line-based measurement is designated (step S140). In this case, the measurement point may be designated in units of subpixels using image enlarging and displaying functions together. In the processing method described above, three-dimensional coordinates corresponding to at least some or all points constituting the reference edge are calculated between the reference edge being decision and the user designating the measurement point, and this is performed until the calculation of the reference line in some cases. Thus, the calculation of the three-dimensional coordinate or the reference line is performed while the user is performing the designation of the measurement point, thereby reducing a waiting time of processing felt by the user.

When a processing system incapable of performing the concurrent process as described above is used, the process is performed, for example, in order of steps S140, S130 and S135 after the reference edge is decided. If the process is performed in this order, a manipulation for deciding the reference edge and a manipulation for designating the measurement point are continuously performed and there is no waiting time between the manipulations due to processing of step S130 and S135. Therefore, the manipulation for deciding the reference edge and the manipulation for designating the measurement point are not divided by the waiting time of processing, thereby reducing a waiting time of processing felt by the user during the manipulation.

Figure 11:
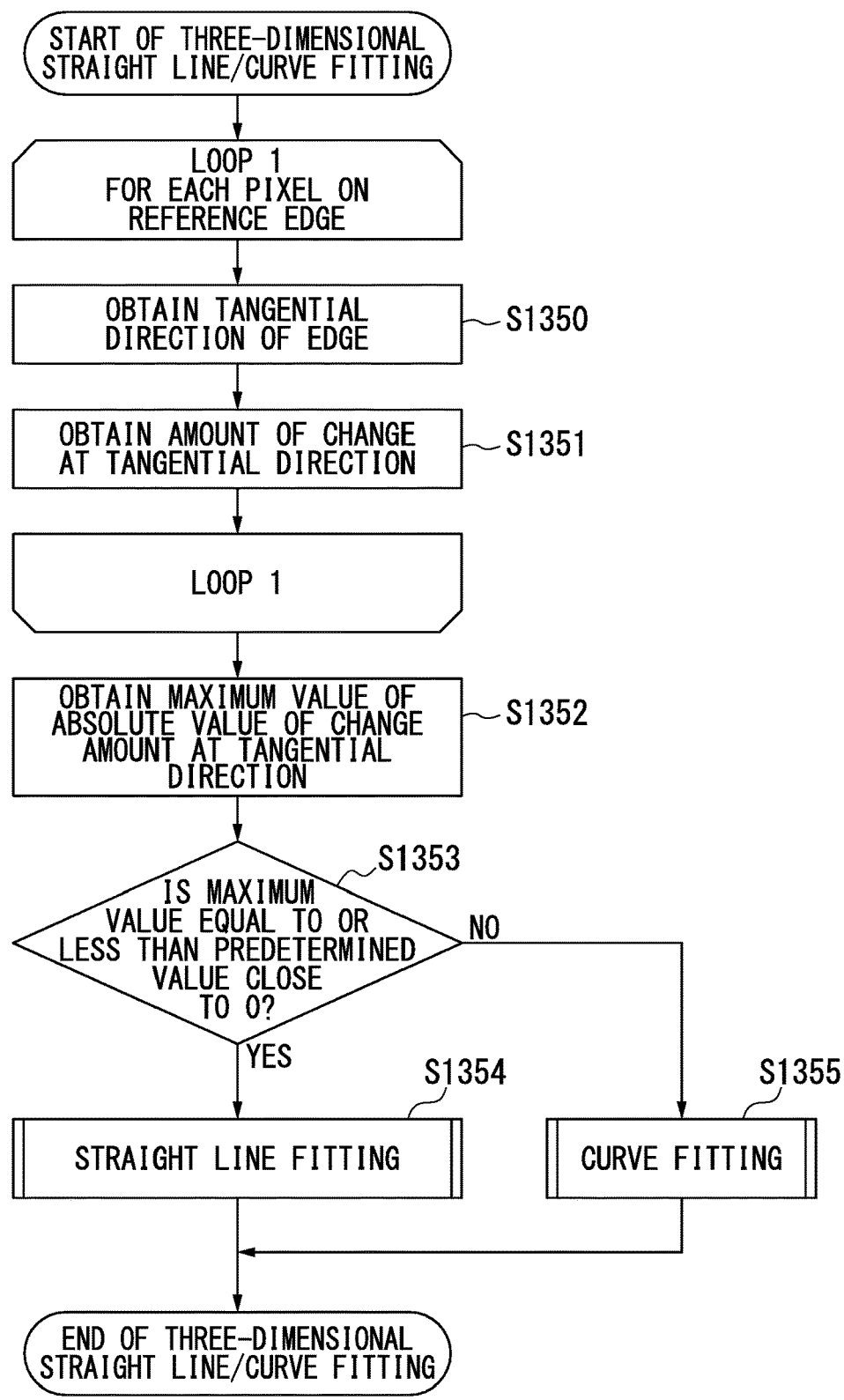
FIG. 11 is a flowchart illustrating a flow of a three-dimensional straight line/curve fitting process according to the embodiment of the present invention.

FIG. 11 illustrates a flow of a three-dimensional straight line/curve fitting process in step S135. The reference line calculation unit 186 performs a process of steps S1350 and S1351 on all the points (pixels) constituting the reference edge. First, the reference line calculation unit 186 obtains a tangential direction of the edge at each of the points constituting the reference edge (step S1350), and obtains an amount of change of a tangential direction at each point from the tangential directions at points on both sides of each point on the reference edge (step S1351). For example, when three points A, B and C are arranged in this order on the edge, an amount of change of the tangential direction at the point B from the tangential direction at the points A and C is obtained.

After a process of steps S1350 and S1351 are performed on all the points constituting the reference edge, the reference line calculation unit 186 obtains a maximum value of absolute values of amounts of change of the tangential directions at the respective points constituting the reference edge (step S1352). The reference line calculation unit 186 then determines whether the obtained maximum value is equal to or less than a predetermined value (step S1353). The predetermined value used for the determination in step S1353 is a value close to 0.

When the maximum value is equal to or less than the predetermined value, the reference edge may be considered as a straight line, and the reference line calculation unit 186 performs straight line fitting to apply a straight line on a space to the edge point group obtained in step S130 and calculates an equation of the straight line (step S1354). Further, when the maximum value exceeds the predetermined value, the reference line calculation unit 186 performs curve fitting to apply a curve on the space to the edge point group obtained in step S130 and calculates an equation of the curve (step S1355). If the straight line fitting of step S1354 or the curve fitting of step S1355 ends, the three-dimensional straight line/curve fitting process ends.

Figure 12:
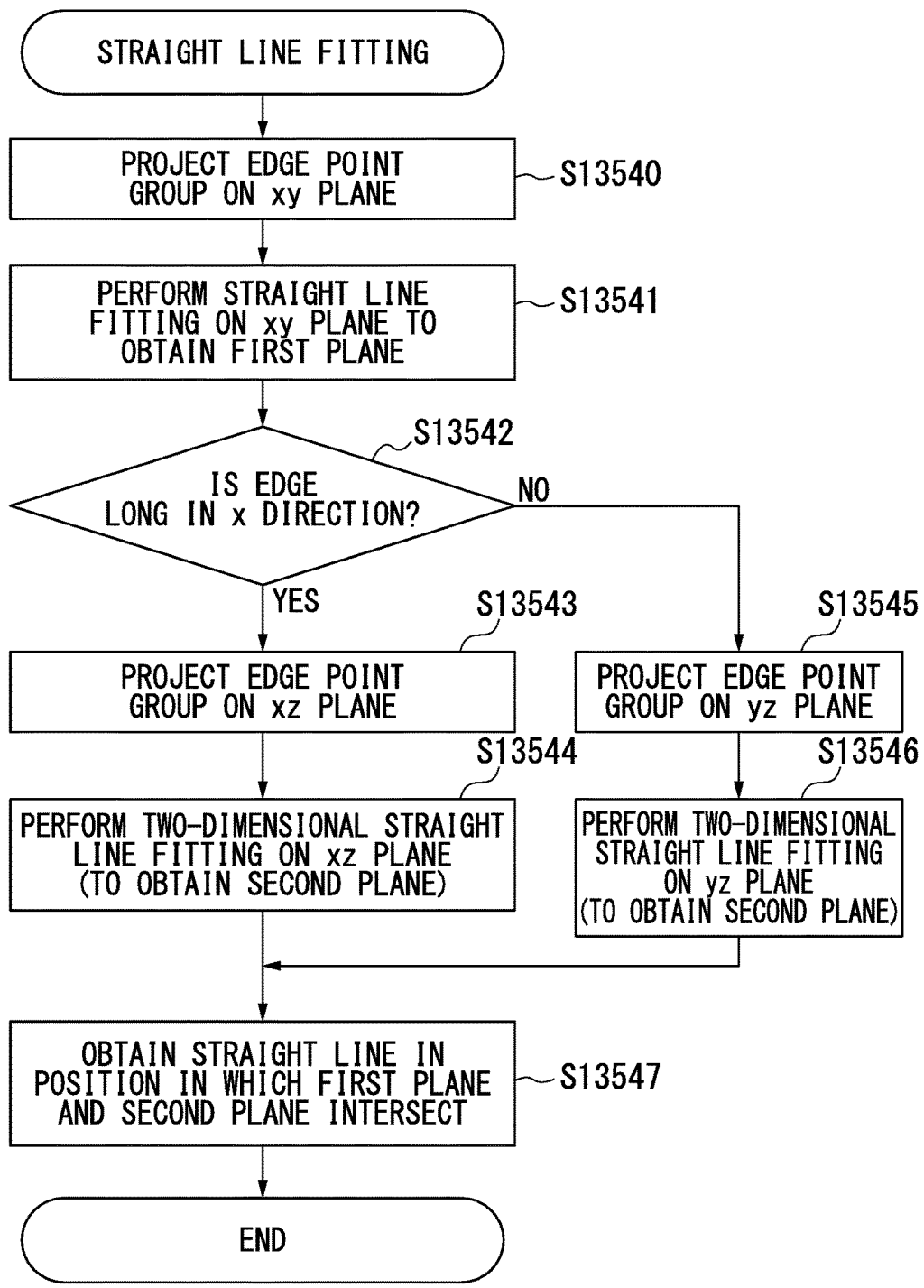
FIG. 12 is a flowchart illustrating a flow of a straight line fitting process according to the embodiment of the present invention.

FIG. 12 illustrates a flow of a straight line fitting process in step S1354. The reference line calculation unit 186 projects the three-dimensional coordinates constituting the edge point group on the xy plane (step S13540). The reference line calculation unit 186 then applies a straight line to each coordinate projected on the xy plane to calculate the equation of the straight line using a least square method on the xy plane (step S13541). The equation calculated in step S13541 is the same as an equation of a plane perpendicular to the xy plane and passing through the reference edge (hereinafter referred to as a first plane).

The reference line calculation unit 186 then determines whether the edge is long in the x direction based on each coordinate projected on the xy plane (step S13542). For example, if an absolute value of a difference between a maximum value and a minimum value of the x coordinate is equal to or more than a predetermined value, it is determined that the edge is long in the x direction. If the absolute value of the difference between the maximum value and the minimum value of the x coordinate is less than the predetermined value, it is determined that the edge is not long in the x direction.

When it is determined that the edge is long in the x direction, the reference line calculation unit 186 projects the three-dimensional coordinates constituting the edge point group on the xz plane (step S13543). The reference line calculation unit 186 then applies a straight line to each coordinate projected on the xz plane to calculate the equation of the straight line using a least square method on the xz plane (step S13544). The calculation of the equation of the straight line in step S13544 is the same as obtaining a plane perpendicular to the xz plane and passing through the reference edge (hereinafter referred to as a second plane).

When it is determined that the edge is not long in the x direction, the reference line calculation unit 186 projects the three-dimensional coordinates constituting the edge point group on a yz plane (step S13545). The reference line calculation unit 186 then applies a straight line to each coordinate projected on the yz plane to calculate the equation of the straight line using a least square method on the yz plane (step S13546). The calculation of the equation of the straight line in step S13566 is the same as obtaining a plane perpendicular to the yz plane and passing through the reference edge (hereinafter referred to as a second plane).

After obtaining the equation of the straight line in step S13544 or step S13546, the reference line calculation unit 186 obtains a straight line in a position in which the first plane and the second plane intersect (step S13547). More specifically, in step S13547, the following process is performed. When the equation of the straight line is obtained in step S13544, the reference line calculation unit 186 obtains a point through which the straight line passes by setting x to 0 in the obtained equation of the straight line. Alternatively, when the equation of the straight line is obtained in step S13546, the reference line calculation unit 186 obtains a point through which the straight line passes by setting y to 0 in the obtained equation of the straight line. The reference line calculation unit 186 then obtains a vector (cross product) orthogonal to each of normal vectors of the first plane and the second plane. The obtained vector is a direction vector, and the straight line passing through the point is a straight line in the position in which the first plane and the second plane intersect. When the straight line in the position in which the first plane and the second plane intersect is obtained, the straight line fitting process ends.

Figure 13:
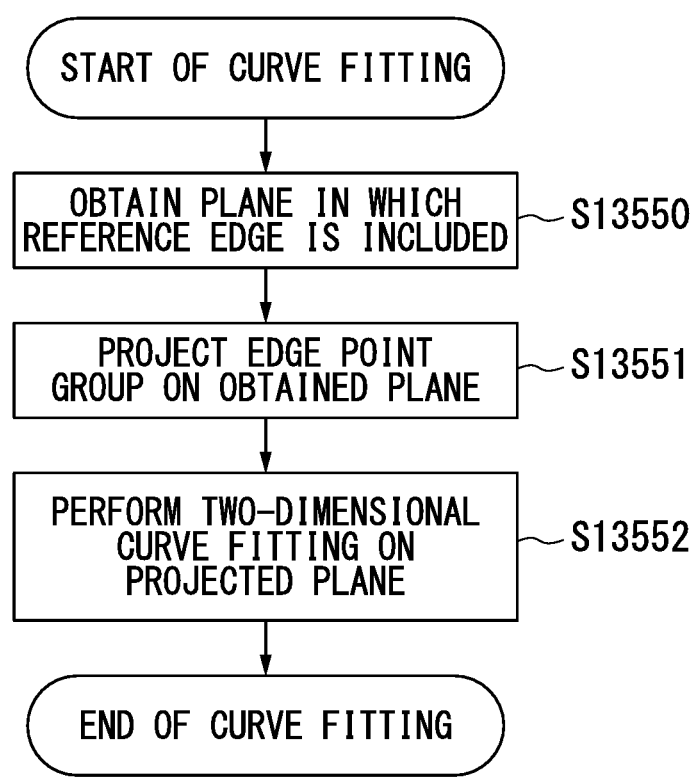
FIG. 13 is a flowchart illustrating a flow of a curve fitting process according to the embodiment of the present invention.

FIG. 13 illustrates a flow of the curve fitting process in step S1355. The reference line calculation unit 186 obtains a plane in which the reference edge is included (step S13550). More specifically, the following process is performed in step S13550. The reference line calculation unit 186 calculates two vectors from the three-dimensional coordinates corresponding to three points at both ends and a center of the reference edge among the three-dimensional coordinates constituting the edge point group. The two vectors are a vector passing through the points at the one end and the center of the reference edge and a vector passing through the points at the other end and the center of the reference edge. The reference line calculation unit 186 then obtains a vector (cross product) orthogonal to the two vectors. The reference line calculation unit 186 then calculates a plane passing through the three-dimensional coordinates corresponding to any of the three points and having the obtained vector as a normal vector.

After obtaining the plane in which the reference edge is included, the reference line calculation unit 186 projects the three-dimensional coordinates constituting the edge point group on the obtained plane (step S13551). The reference line calculation unit 186 then applies a curve to each projected coordinate to calculate an equation of the curve (step S13552). A specific curve fitting method is described, for example, in Japanese Unexamined Patent Application, First Publication No. 2005-204724. If the equation of the curve is obtained, the curve fitting process ends.

When the calculation of the reference line (step S135) and the designation of the measurement point (step S140) end, the three-dimensional distance calculation unit 188 calculates a three-dimensional distance between the three-dimensional coordinates corresponding to the measurement point and the three-dimensional reference line (step S145). When the reference line is represented by a straight line, the three-dimensional distance is calculated as follows. If a coordinate of the point O is $(x_0, y_0, z_0)$ and a component of the direction vector of the three-dimensional straight line L passing through the point O is $(a, b, c)$, a coordinate $(x, y, z)$ of a point on the straight line L is represented by the following Equations (12) to (14) using a parameter t.

$$x = x_0 + at \quad (12)$$

$$y = y_0 + bt \quad (13)$$

$$z = z_0 + ct \quad (14)$$

In this case, a coordinate $(x_H, y_H, z_H)$ of a foot H of a perpendicular taken down from a point M not on the straight line L to the straight line L, with a coordinate of the point M being $(x_M, y_M, z_M)$, is represented by the following Equations (15) to (17) using a parameter $t_H$.

$$x_H = x_0 + at_H \quad (15)$$

$$y_H = y_0 + bt_H \quad (16)$$

$$z_H = z_0 + ct_H \quad (17)$$

Since the vector OH and the vector MH are orthogonal to each other, the parameter $t_H$ is obtained as shown in the following Equation (18).

$$t_H = \frac{a(x_M - x_0) + b(y_M - y_0) + c(z_M - z_0)}{a^2 + b^2 + c^2} \quad (18)$$

Therefore, a distance d between the point M and the straight line L is obtained by the following Equation (19).

$$d = \sqrt{(x_M - x_H)^2 + (y_M - y_H)^2 + (z_M - z_H)^2} \quad (19)$$

The three-dimensional distance when the reference line is represented by a curve is disclosed in Japanese Unexamined Patent Application Publication No. 2005-204724 described above.

When the three-dimensional distance is calculated, the display control unit 183 generates a graphic image signal for causing a value of the calculated three-dimensional distance to be displayed as a measurement result on the monitor 4, and outputs the graphic image signal to the video signal processing circuit 12. Accordingly, the value of the three-dimensional distance is displayed on the monitor 4 (step S150). The user can confirm the measurement result based on the value displayed on the monitor 4. If the value of the three-dimensional distance is displayed on the monitor 4, the line-based measurement ends.

As described above, according to the present embodiment, since manipulations necessary to set the reference line may be only the manipulation for designating one reference point to set the edge extraction region, and the manipulation for selecting the reference edge from among the plurality of extracted edges, time and effort of the manipulations related to the setting of the reference line can be reduced and time necessary for line-based measurement can be shortened.

Further, when the edge presented as the reference edge corresponding to the reference line is not a desired edge, the edge can be easily switched to another edge. For example, when there is a difference of brightness and darkness between the subject and a background, an edge which the user desires to select as the reference edge is on a surface of the subject, and a difference of brightness and darkness in the vicinity of the edge is relatively small, an edge in highest order among automatically extracted edges is likely to be a border between the subject and the background. Even in this case, the edge can be easily switched such that the desired edge can be selected as the reference edge.

Further, one index for selecting an edge which is the reference edge can be presented to the user by displaying the information of an order of the plurality of extracted edges.

Further, since the three-dimensional coordinates are calculated for only points constituting the decided reference edge, a calculation amount of the entire process can be reduced.

While the edge to be selected as the reference edge is switched based on the instruction from the user in the description described above, the edge to be selected as the reference edge may be automatically switched. For example, when the edge to be selected as the reference edge is switched sequentially at predetermined time intervals and the user performs a decision manipulation, the edge selected as the reference edge at that time point is decided as the reference edge. In this case, since a manipulation necessary to select the reference edge is only a manipulation for deciding the reference edge, time and effort of the manipulation can be further reduced.

Figure 14:
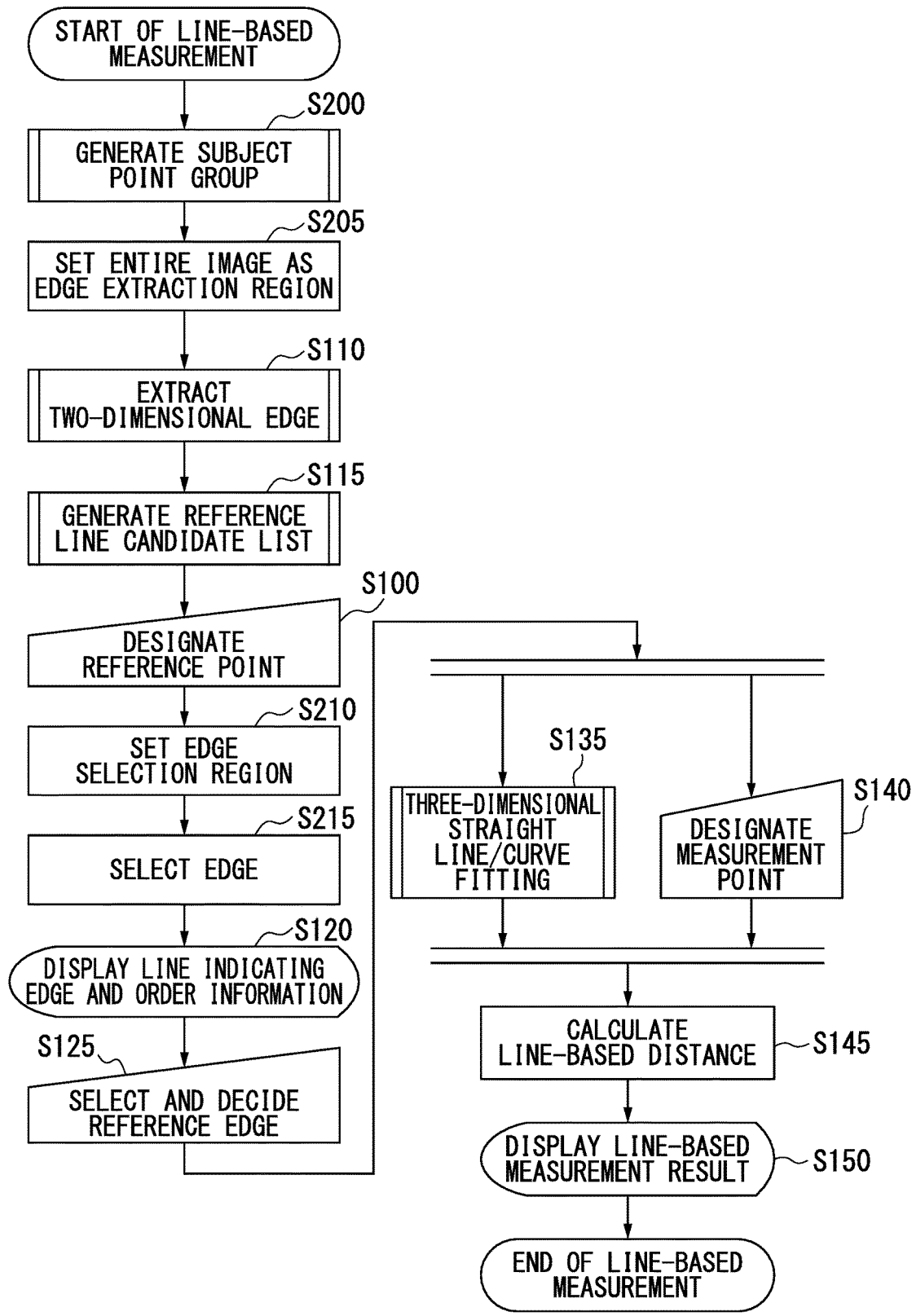
FIG. 14 is a flowchart illustrating a flow of a line-based measurement process according to another embodiment of the present invention.

Next, another embodiment of the present invention will be described. FIG. 14 illustrates a flow of a process in line-based measurement of the present embodiment. The same processes as those shown in FIG. 8 among the processes shown in FIG. 14 are denoted by the same reference numerals. If line-based measurement is initiated after a still image of a subject is acquired according to an instruction from a user, the three-dimensional coordinate calculation unit 185 calculates a three-dimensional coordinate corresponding to each of points (pixels) included in a first range in the image of the subject, and generates a subject point group consisting of three-dimensional coordinates of the respective points (step S200).

Figure 15:
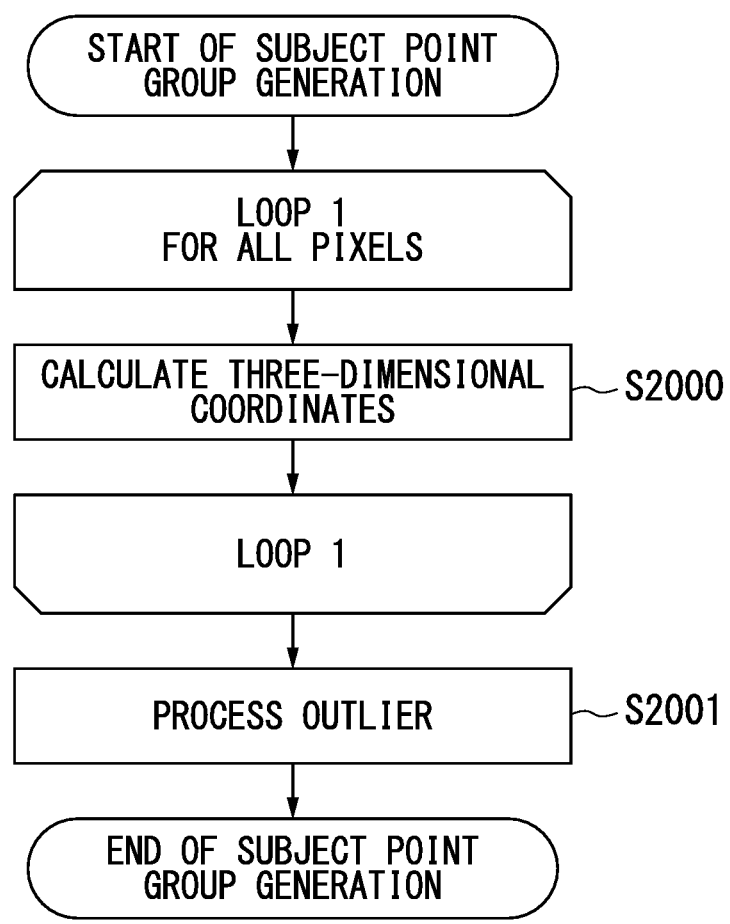
FIG. 15 is a flowchart illustrating a flow of a process of generating a subject point group according to the embodiment of the present invention.

FIG. 15 illustrates a flow of the process of generating the subject point group in step S200.

The three-dimensional coordinate calculation unit 185 calculates the three-dimensional coordinate corresponding to each of all the points included in the first range in the image of the subject (step S2000). In the present embodiment, the first range for which the three-dimensional coordinates are calculated is the entire image of the subject. The first range includes at least a second range that is set in the edge extraction region in step S205. Information indicating the first range is, for example, recorded in a program for measurement executed by the CPU 18, but the first range may be changed by an instruction from the user. After the process of step S2000 has been performed on all the points included in the entire image of the subject, the three-dimensional coordinate calculation unit 185 corrects outliers for the calculated three-dimensional coordinates by replacing three-dimensional coordinates far apart from the three-dimensional coordinates of neighboring points with an average value of the three-dimensional coordinates of the neighboring points, for example, using a median filter (step S2001). If the correction of the outliers ends, the process of generating the subject point group ends.

After the process of generating the subject point group ends, the region-setting unit 181 sets the second range in the image of the subject, in the edge extraction region (step S205). In the present embodiment, the second range in which the edge extraction region is set is the entire image of the subject. Information indicating the second range is, for example, recorded in the program for measurement executed by the CPU 18, but the second range may be changed according to an instruction from the user. If the edge extraction region is set, the edge extraction unit 182 performs two-dimensional edge extraction (step S110). The two-dimensional edge extraction process is the same as the process shown in FIG. 9. However, two-dimensional coordinates of points constituting each edge included in the edge data of the present embodiment are associated with the three-dimensional coordinates constituting the subject point group. Both the two-dimensional coordinates and the three-dimensional coordinates of the points constituting each edge may be included in the edge data. If the two-dimensional edge extraction process ends, the edge extraction unit 182 generates a reference line candidate list (step S115). A process of generating the reference line candidate list is the same as the process shown in FIG. 10.

If the process of generating the reference line candidate list ends, the manipulation unit 6 is manipulated by the user and a reference point for setting an edge selection region, which will be described hereinafter, is designated (step S100). If the reference point is designated, the region-setting unit 181 sets the edge selection region based on the reference point in the image (step S210). The edge selection region is a region in which an edge which is a target of a subsequent process is selected from among edges extracted in the entire image of the subject. For example, a region inside a circle whose radius is a predetermined value around the two-dimensional coordinate of the reference point is set as the edge selection region, similar to the edge extraction region described in the above-mentioned embodiment. The edge selection region may be a region set on the basis of the coordinate of the reference point, and is not necessarily a circle.

When the edge included in the reference line candidate list is not in the edge selection region based on the reference point designated by the user, an edge cannot be selected. In this case, a warning may be displayed to cause the user to designate the reference point again, the edge selection region may be gradually expanded until the edge included in the reference line candidate list is found, or the edge selection region may be moved to a position overlapping a nearest edge among the edges included in the reference line candidate list.

If the edge selection region is set, the edge selection unit 184 selects an edge overlapping the selection region (an edge at least partially included in the selection region (passing through the selection region)) from among edges based on edge data, and uses the selected edge as a reference edge selection target (step S215). In this case, in the reference line candidate list, information other than the selection target edge may be erased or a flag indicating that the edge is a selection target may be given to information of the selection target edge.

If the edge which is the reference edge selection target is selected, the display control unit 183 generates a graphic image signal for causing the line indicating each edge of the selection target and the order information to be displayed on the monitor 4 based on the edge data and the reference line candidate list, and outputs the graphic image signal to the video signal processing circuit 12. Accordingly, the line indicating each edge of the selection target and the order information are displayed on the monitor 4 to be superimposed on the image (step S120).

After the line indicating each edge of the selection target and the order information are displayed, the manipulation unit 6 is manipulated by the user and the reference edge is selected. In this case, the user can switch the edge to be selected as the reference edge, as described in the above-mentioned embodiment. If a decision manipulation is performed by the user in a state in which a desired edge has been selected as the reference edge, the reference edge is decided (step S125).

After the reference edge is decided, a process of step S135 and a process of step S140 are performed concurrently. The reference line calculation unit 186 performs three-dimensional straight line/curve fitting to apply a straight line or a curve on a space to the edge point group and calculates an equation (approximation equation) of the straight line or the curve (step S135). The calculated straight line or curve is a reference line. The three-dimensional straight line/curve fitting process is the same as the process shown in FIG. 11. In parallel with the process of step S135, the manipulation unit 6 is manipulated by the user and the measurement point in the line-based measurement is designated (step S140).

When the calculation of the reference line (step S135) and the designation of the measurement point (step S140) end, the three-dimensional distance calculation unit 188 calculates a three-dimensional distance between the three-dimensional coordinate corresponding to the measurement point and the three-dimensional reference line (step S145). If the three-dimensional distance is calculated, the display control unit 183 generates a graphic image signal for causing a value of the calculated three-dimensional distance to be displayed as a measurement result on the monitor 4, and outputs the graphic image signal to the video signal processing circuit 12. Accordingly, the value of the three-dimensional distance is displayed on the monitor 4 (step S150). If the value of the three-dimensional distance is displayed on the monitor 4, the line-based measurement ends.

The line-based measurement process (FIG. 14) in the present embodiment is initiated at a time point which an instruction to start up a line-based measurement function is input by the user or at a time point earlier than such a time point, which is a time point at which an instruction to acquire a still image displayed on the monitor 4 is input by the user. Each of the instruction to start up the line-based measurement function and the instruction to display the still image on the monitor 4 may be input by a manipulation of the manipulation unit 6.

As described above, according to the present embodiment, the edge extraction region is automatically set in a predetermined region in the image of the subject. Accordingly, since manipulations necessary to set the reference line may be only a manipulation for designating one reference point to set the edge selection region, and a manipulation for selecting the reference edge from among a plurality of edges passing through the edge selection region, time and effort of the manipulation related to the setting of the reference line can be reduced and a time necessary for the line-based measurement can be shortened.

Further, since the three-dimensional coordinates corresponding to all points included in the predetermined range in the image of the subject are calculated immediately after the line-based measurement process is initiated, a calculation amount after the reference edge is decided can be reduced. Therefore, a waiting time for processing felt by the user after the reference edge has been decided can be reduced.

Immediately after the line-based measurement process is initiated, the user views an image to perform confirmation of the subject, performs a manipulation for recording the image data, or plays back past acquired image data to compare a current image with the past image. The waiting time for processing felt by the user throughout the line-based measurement can be reduced by calculating the three-dimensional coordinates corresponding to all the points included in the predetermined range in the image of the subject as described above while the user is performing any of such actions.

Further, only the edge overlapping the edge selection region based on the reference point designated by the user among the edges extracted from the predetermined range in the image of the subject is a candidate of the reference edge. Therefore, the user can efficiently select the reference edge even when a number of edges are extracted from the predetermined range in the image of the subject.

While the edge selection region is set in the description described above, all the edges extracted from the edge extraction region may be reference edge selection targets without setting the edge selection region. For example, when the number of edges extracted from the edge extraction region is equal to or more than a predetermined value, the edge selection region may be set and when the number of edges is less than the predetermined value, the edge selection region may not be set. Since the manipulation of the user for designating the reference point is omitted when the edge selection region is not set, time and effort of the manipulation can be further reduced.

Figure 16:
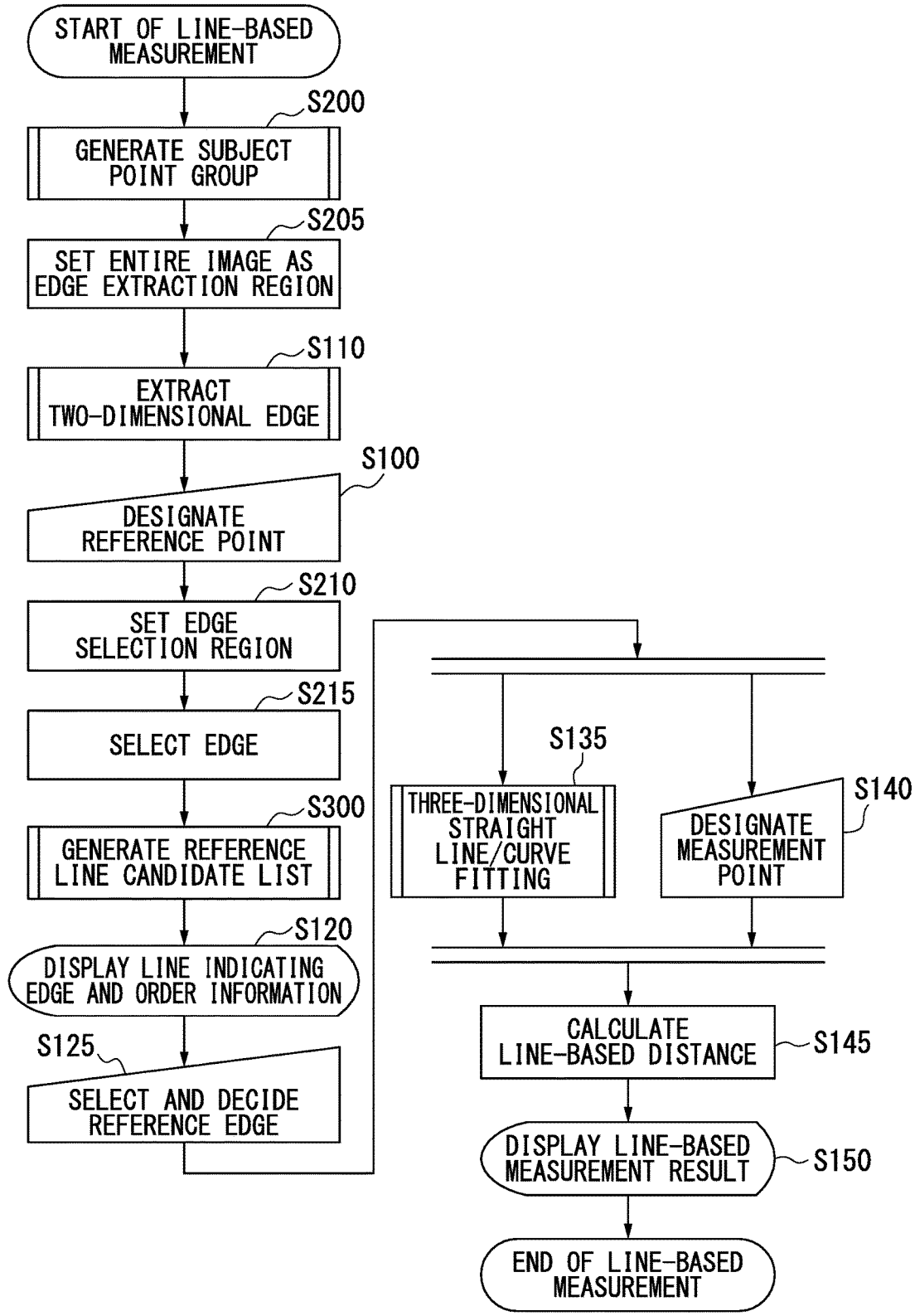
FIG. 16 is a flowchart illustrating a flow of a line-based measurement process according to another embodiment of the present invention.

Next, another embodiment of the present invention will be described. FIG. 16 illustrates a flow of a process in line-based measurement of the present embodiment. Among processes shown in FIG. 16, processes that are the same as those shown in FIG. 14 are denoted by the same reference numerals. Hereinafter, a difference with the processes shown in FIG. 14 will be mainly described. In the process shown in FIG. 16, after the two-dimensional edge extraction (step S110) is performed, the manipulation unit 6 is manipulated by a user and a reference point that is a reference for setting the edge selection region is designated (step S100).

If the reference point is designated, the edge selection region is set in an image (step S210), and an edge overlapping the selection region (an edge at least partially included in the selection region (passing through the selection region)) is selected from among edges (step S215). If an edge that is a reference edge selection target is selected, the reference line candidate list is generated (step S300).

Figure 17:
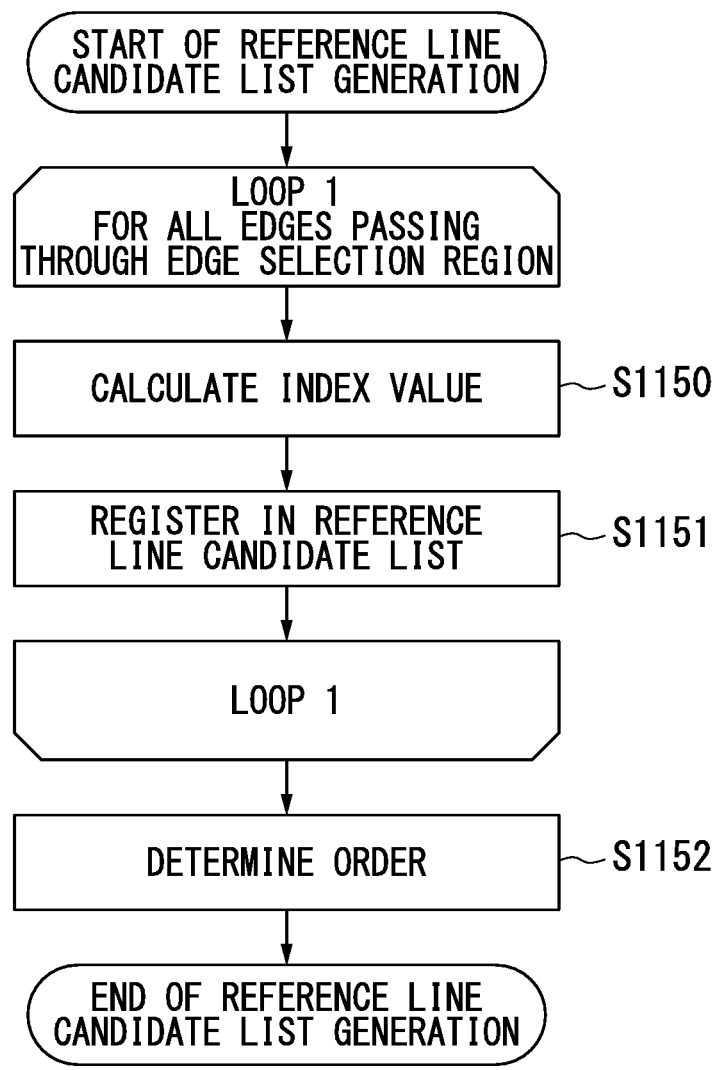
FIG. 17 is a flowchart illustrating a flow of a process of generating a reference line candidate list according to the embodiment of the present invention.

FIG. 17 illustrates a flow of the process of generating a reference line candidate list in step S300. Respective processes of steps S1150 to S1152 are the same as those in FIG. 10, but differ in that each process is performed by the edge selection unit 184 and that the processes of steps S1150 and S1151 are performed on all edges passing through the edge selection region set in step S210.

If the reference line candidate list is generated, the display control unit 183 generates a graphic image signal for causing a line indicating each edge of a selection target and order information to be displayed on the monitor 4, based on the edge data and the reference line candidate list, and outputs the graphic image signal to the video signal processing circuit 12. Accordingly, the line indicating each edge of the selection target and the order information are displayed on the monitor 4 to be superimposed on the image (step S120). A subsequent process is the same as the process shown in FIG. 14.

In the process shown in FIG. 14, since the edge extraction is performed on the entire image of the subject in step S110, a number of edges are likely to be extracted in some cases. In step S115, a process including calculation of index values is performed on all the edges extracted from the entire image of the subject. Accordingly, when a number of edges are extracted, a waiting time of processing felt by the user increases.

Meanwhile, in the process shown in FIG. 16, since the process including the calculation of index values is performed in step S300 on the edge selected in step S215 among the edges extracted in step S110, a time for calculating the index values can be shortened in comparison with the process shown in FIG. 14 even when a number of edges are extracted in step S110. Therefore, according to the present embodiment, a waiting time of processing felt by the user can be reduced in comparison with the above-mentioned embodiment.

Figure 18:
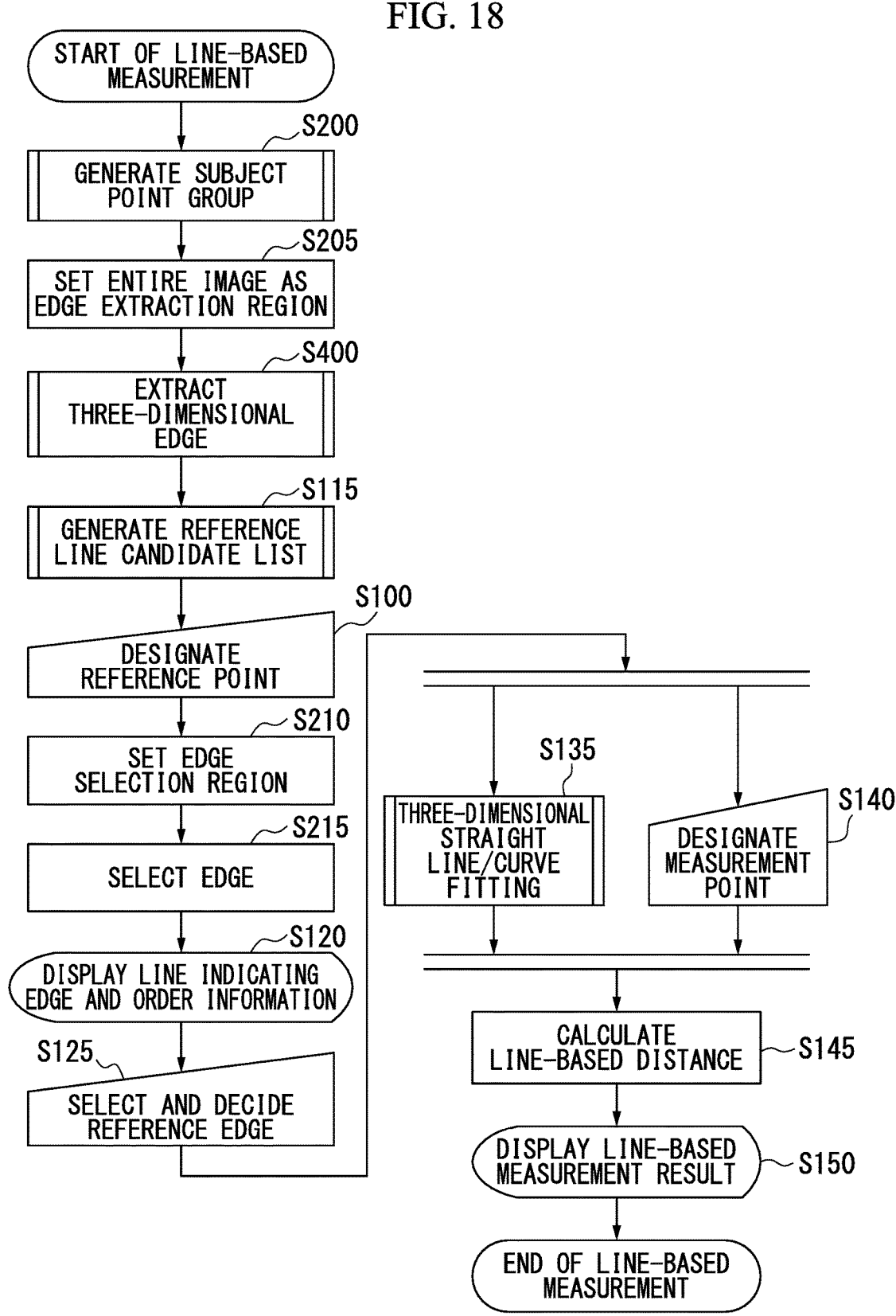
FIG. 18 is a flowchart illustrating a flow of a line-based measurement process according to another embodiment of the present invention.

Next, another embodiment of the present invention will be described. FIG. 18 illustrates a flow of a process in the line-based measurement of the present embodiment. In the process shown in FIG. 18, the same processes as the processes shown in FIG. 14 are denoted by the same reference numerals. Hereinafter, a difference with the processes shown in FIG. 14 will be described.

Figure 19:
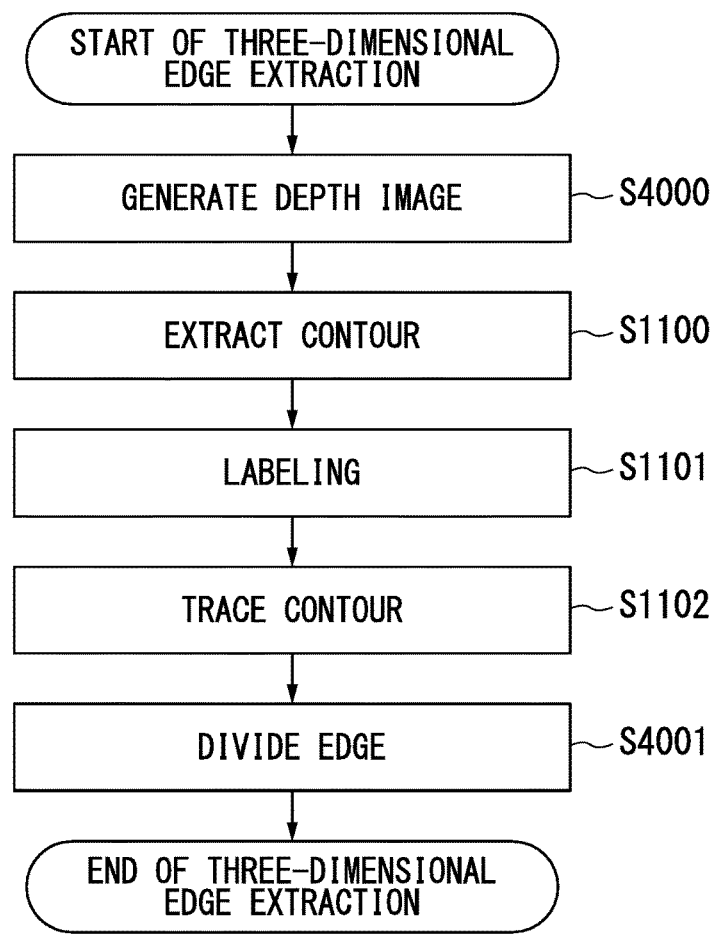
FIG. 19 is a flowchart illustrating a flow of a three-dimensional edge extraction process according to the embodiment of the present invention.

In the process shown in FIG. 18, the edge extraction unit 182 performs three-dimensional edge extraction instead of the two-dimensional edge extraction (step S110 in FIG. 14) (step S400). FIG. 19 illustrates a flow of a three-dimensional edge extraction process in step S400. The edge extraction unit 182 generates a depth image from the image of the subject (step S4000). The depth image is an image having a z-coordinate (corresponding to a distance from the imaging element 28 or the imaging optical system to the subject) constituting the three-dimensional coordinate of each of the points in the entire image of the subject calculated in step S200 as a pixel value.

A process of steps S1100 to S1102 after the depth image has been generated is the same as the process of steps S1100 to S1102 shown in FIG. 9 except that an image as a processing target is the depth image. After contour tracing is performed in step S1102 and an edge of an extension portion of the edge extracted in step S1100 is extracted, the edge extraction unit 182 divides the edges extracted in steps S1100 and S1102 (step S4001). Hereinafter, details of the process of dividing an edge will be described.

In the division of the edge, the process is performed using the three-dimensional coordinates of each point on the edge. When the edge is divided, the edge extraction unit 182 obtains a tangential direction of the edge at each point on the edge and obtains a vector indicating a change of the tangential direction at each point from tangential directions at points at both sides of each point on the edge. If a unit vector parallel to a tangential direction at any point i on the edge is $q_i$, a vector indicating the change of the tangential direction at the point i is $p_i$, and the points on both sides of the point i are a point i−1 and a point i+1, the vector $p_i$ indicating the change of the tangential direction is represented by Equation (11) described above.

The edge extraction unit 182 divides the edge at a point at which a magnitude of the vector indicating the change of the tangential direction at each point on the edge exceeds a predetermined value, a point at which a direction of a projection vector obtained by projecting the vector indicating the change of the tangential direction on a plane perpendicular to the tangential direction is reversed, or a point at which the direction of the projection vector is changed. Hereinafter, a projection vector will be described.

If a unit vector parallel to the tangential direction at any point i on the edge is $u_i$ and a magnitude of a vector $q_i$ parallel to the tangential direction at the point i is $|q_i|$, the unit vector $u_i$ is represented by the following Equation (20).

$$u_i = q_i / |q_i| \qquad (20)$$

If a vector obtained by projecting the vector $p_i$ on a plane perpendicular to the tangential direction at the point i is $v_i$ and a dot product of the vector $q_i$ and the vector $u_i$ is $(q_i \cdot u_i)$, the vector $v_i$ is represented by the following Equation (21).

$$v_i = p_i - (p_i - (p_i \cdot u_i) u_i \qquad (21)$$

The divided edges are different edges, and a different label is given to each edge. Here, a point belonging to each divided edge is in the same plane, and the edges have no inflection points. The edge data for managing coordinates of points constituting the edge and the label of the edge is updated to be data corresponding to each divided edge. If the edge is divided, the three-dimensional edge extraction process ends. A subsequent process is the same as the process shown in FIG. 14.

In two-dimensional edge extraction, a pattern on the plane may be detected as an edge. For example, this is effective for measurement of an amount of coating protruding from a border or measurement of an erosion amount of rust eroded from a joint of a part or the like.

Meanwhile, in the three-dimensional edge extraction, the edge can be detected even when there is no change in brightness in the image, the change in brightness is small, or the edge is shown not to exist. For example, an edge of a rounded surface having no shadow can be detected through adjustment of illumination. Further, there is a characteristic in that a simple pattern is not erroneously detected as the edge. For example, an edge is not erroneously detected for a subject of a material with fiber on its surface like CFRP (carbon fiber reinforced plastic).

While the case in which the two-dimensional edge extraction in the process shown in FIG. 14 is replaced with the three-dimensional edge extraction has been described in the present embodiment, the two-dimensional edge extraction in the process shown in FIG. 16 may be replaced with the three-dimensional edge extraction.

(Modification)

Figure 20:
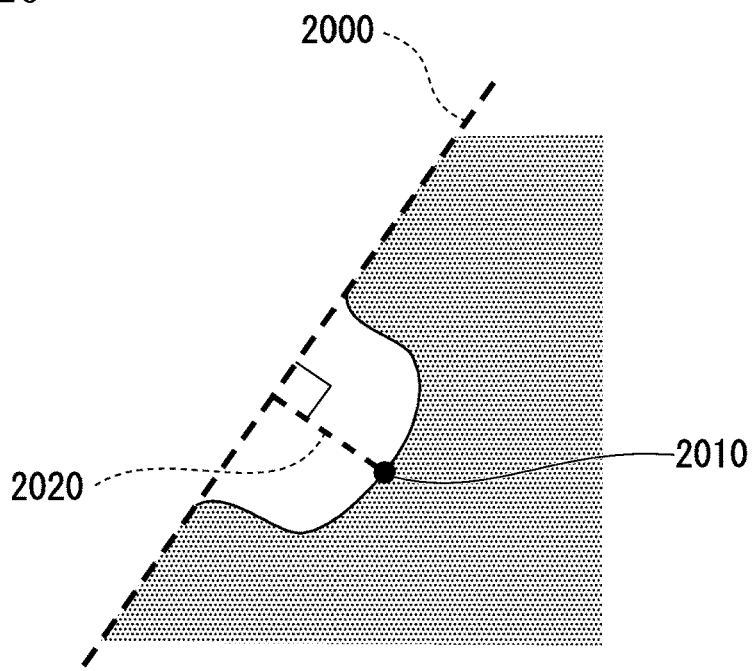
FIG. 20 is a reference diagram illustrating an example of a subject that is a line-based measurement target.

Next, a variant applicable to each of the embodiments described above will be described. The line-based measurement may also be performed on a subject of which the surface is partially lacking, as shown in FIG. 20. If an edge corresponding to a line 2000 is selected as a reference edge and a measurement point 2010 is designated, a three-dimensional distance (a three-dimensional distance corresponding to a length of a line 2020) between a reference line on a space corresponding to the reference edge and a three-dimensional coordinate corresponding to the measurement point 2010 is calculated.

When a user selects the reference edge, a line indicating an edge selected as the reference edge among lines of edges to be displayed on the monitor 4 and lines indicating other edges may be distinguished using thicknesses or colors of the lines. Further, only the line indicating the edge selected as the reference edge may flash.

When the user selects the reference edge, information corresponding to the edge selected as the reference edge in order information to be displayed on the monitor 4 and information corresponding to the other edges may be distinguished using colors of icons or colors and thicknesses of letters in the icons. Further, only the icon indicating the information corresponding to the edge selected as the reference edge may flash.

When the edge cannot be extracted in the edge extraction region, a threshold in the edge extraction may be decreased and then the edge extraction may be performed again or the edge extraction region may be automatically expanded and then the edge extraction may be performed again.

The measurement point in the line-based measurement may be set automatically. For example, a vertex of a contour of a pattern may be detected through image processing and set as the measurement point.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. An endoscope device comprising:
an insertion portion;
an imaging element that generates an image based on a subject image formed through an optical system of the insertion portion;
a monitor for displaying the image;
an interface device that accepts input from a user;
a memory having a measurement program stored thereon; and
a processor that, under control of the measurement program stored in the memory, is configured to:
obtain the image from the imaging element;
display the obtained image on the monitor;
set, on the displayed image, an edge extraction region;
extract a plurality of edges from within an area of the edge extraction region set on the displayed image;
display a first graphic indicating the plurality of extracted edges such that the first graphic is superimposed on the displayed image;
after extracting the plurality of edges, set, according to an input from the interface device, a reference point on the displayed image on which the first graphic is superimposed;

set, on the displayed image, a region based on the reference point as an edge selection region, the edge selection region being set to be smaller than the edge extraction region;

identify edges that are included within the edge selection region, from among the plurality of extracted edges;

select, according to an input from the interface device, one edge from among the edges identified as being included within the edge selection region as a reference line;

display a second graphic indicating the selected reference line such that the second graphic is superimposed on the displayed image;

set, according to an input from the interface device, a measurement point in the displayed image;

calculate a spatial distance between the measurement point and the reference line; and display, on the monitor, a third graphic indicating a value of the spatial distance having been calculated.

2. The endoscope device according to claim 1, wherein, when it is impossible to select an edge overlapping the edge selection region from within the edge selection region, the processor gradually expands the edge selection region until it is possible to select an edge overlapping the edge selection region.

3. The endoscope device according to claim 1, wherein, when it is impossible to select an edge overlapping the edge selection region from within the edge selection region, the processor moves the edge selection region to a position at which an edge nearest to the edge selection region overlaps the edge selection region.

4. The endoscope device according to claim 1, wherein:
the processor generates a reference line candidate list in which information regarding each of the extracted edges is registered, and
when an edge overlapping the edge selection region is selected from within the edge selection region as the one edge, the processor deletes information regarding edges other than the one edge from the reference line candidate list.

5. The endoscope device according to claim 1, wherein:
the processor generates a reference line candidate list in which information regarding each of the extracted edges is registered, and
when an edge overlapping the edge selection region is selected from within the edge selection region as the one edge, the processor assigns a flag indicating that the one edge is a selection target to information regarding the one edge in the reference line candidate list.

6. A non-transitory computer-readable medium having stored thereon a measurement program that is executable by a processor of an endoscope device, the endoscope device further comprising an insertion portion, an imaging element that generates an image based on a subject image formed through an optical system of the insertion portion, a monitor for displaying the image, and an interface device that accepts input from a user, and the measurement program being executable by the processor to cause the processor to perform functions comprising:
obtaining the image from the imaging element;
displaying the obtained image on the monitor;
setting, on the displayed image, an edge extraction region;
extracting a plurality of edges from within an area of the edge extraction region set on the displayed image;
displaying a first graphic indicating the plurality of extracted edges such that the first graphic is superimposed on the displayed image;
after extracting the plurality of edges, setting, according to an input from the interface device, a reference point on the displayed image on which the first graphic is superimposed;
setting, on the displayed image, a region based on the reference point as an edge selection region, the edge selection region being set to be smaller than the edge extraction region;
identifying edges that are included within the edge selection region, from among the plurality of extracted edges;
selecting, according to an input from the interface device, one edge from among the edges identified as being included within the edge selection region as a reference line;
displaying a second graphic indicating the selected reference line such that the second graphic is superimposed on the displayed image;
setting, according to an input from the interface device, a measurement point in the displayed image;
calculating a spatial distance between the measurement point and the reference line; and
displaying, on the monitor, a third graphic indicating a value of the spatial distance having been calculated.

7. A measurement method for determining a spatial distance executed by a processor of an endoscope device under control of a measurement program stored in a memory, the endoscope device further comprising an insertion portion, an imaging element that generates an image based on a subject image formed through an optical system of the insertion portion, a monitor, and an interface device that accepts input from a user, and the method comprising:
obtaining the image from the imaging element;
displaying the obtained image on the monitor;
setting, on the displayed image, an edge extraction region;
extracting a plurality of edges from within an area of the edge extraction region set on the displayed image;
displaying a first graphic indicating the plurality of extracted edges such that the first graphic is superimposed on the displayed image;
after extracting the plurality of edges, setting, according to an input from the interface device, a reference point on the displayed image on which the first graphic is superimposed;
setting, on the displayed image, a region based on the reference point as an edge selection region, the edge selection region being set to be smaller than the edge extraction region;
identifying edges that are included within the edge selection region, from among the plurality of extracted edges;
selecting, according to an input from the interface device, one edge from among the edges identified as being included within the edge selection region as a reference line;
displaying a second graphic indicating the selected reference line such that the second graphic is superimposed on the displayed image;
setting, according to an input from the interface device, a measurement point in the displayed image;
calculating a spatial distance between the measurement point and the reference line; and displaying, on the monitor, a third graphic indicating a value of the spatial distance having been calculated.

\* \* \* \* \*